US007923429B2

(12) United States Patent
Miller et al.

(10) Patent No.: US 7,923,429 B2
(45) Date of Patent: Apr. 12, 2011

(54) TREATMENT FOR CD5$^+$ B CELL LYMPHOMA

(75) Inventors: Richard L. Miller, Saint Paul, MN (US); David E. Spaner, Saint Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/173,719

(22) Filed: Jul. 15, 2008

(65) Prior Publication Data

US 2009/0017076 A1 Jan. 15, 2009

Related U.S. Application Data

(63) Continuation of application No. 10/933,594, filed on Sep. 3, 2004, now abandoned.

(60) Provisional application No. 60/561,440, filed on Apr. 12, 2004, provisional application No. 60/500,478, filed on Sep. 5, 2003.

(51) Int. Cl.
*A01N 61/00* (2006.01)
*A61K 45/00* (2006.01)

(52) U.S. Cl. ........................................ 514/1; 424/278.1

(58) Field of Classification Search ........................ None
See application file for complete search history.

(56) References Cited

U.S. PATENT DOCUMENTS

| | | | |
|---|---|---|---|
| 3,314,941 | A | 4/1967 | Lundquist, Jr. et al. |
| 3,450,693 | A | 6/1969 | Suzuki et al. |
| 3,670,086 | A | 6/1972 | Pryor et al. |
| 3,692,907 | A | 9/1972 | Fleming et al. |
| 3,891,660 | A | 6/1975 | Denzel et al. |
| 3,899,508 | A | 8/1975 | Wikel |
| 3,917,624 | A | 11/1975 | El-Haj et al. |
| 4,006,237 | A | 2/1977 | Buckle et al. |
| 4,053,588 | A | 10/1977 | Konig et al. |
| 4,381,344 | A | 4/1983 | Rideout et al. |
| 4,552,874 | A | 11/1985 | Mardin et al. |
| 4,563,525 | A | 1/1986 | Campbell, Jr. |
| 4,593,821 | A | 6/1986 | Brule |
| 4,668,686 | A | 5/1987 | Meanwell et al. |
| 4,689,338 | A | 8/1987 | Gerster |
| 4,690,930 | A | 9/1987 | Takada et al. |
| 4,698,346 | A | 10/1987 | Musser et al. |
| 4,698,348 | A | 10/1987 | Gerster |
| 4,753,951 | A | 6/1988 | Takada et al. |
| 4,758,574 | A | 7/1988 | Robertson et al. |
| 4,774,339 | A | 9/1988 | Haugland et al. |
| 4,775,674 | A | 10/1988 | Meanwell et al. |
| 4,800,206 | A | 1/1989 | Alig et al. |
| 4,826,830 | A | 5/1989 | Han et al. |
| 4,837,378 | A | 6/1989 | Borgman |
| 4,880,779 | A | 11/1989 | Gallaher |
| 4,904,669 | A | 2/1990 | Knoll et al. |
| 4,929,624 | A | 5/1990 | Gerster et al. |
| 4,988,714 | A | 1/1991 | Alig et al. |
| 4,988,815 | A | 1/1991 | Andre et al. |
| 5,037,986 | A | 8/1991 | Gerster |
| 5,175,296 | A | 12/1992 | Gerster |
| 5,187,288 | A | 2/1993 | Kang et al. |
| 5,225,183 | A | 7/1993 | Purewal et al. |
| 5,238,944 | A | 8/1993 | Wick et al. |
| 5,248,782 | A | 9/1993 | Haugland et al. |
| 5,266,575 | A | 11/1993 | Gerster et al. |
| 5,268,376 | A | 12/1993 | Gester |
| 5,274,113 | A | 12/1993 | Kang et al. |
| 5,346,905 | A | 9/1994 | Gerster |
| 5,352,680 | A | 10/1994 | Portoghese et al. |
| 5,352,784 | A | 10/1994 | Nikolaides et al. |
| 5,367,076 | A | 11/1994 | Gerster |
| 5,376,501 | A | 12/1994 | Marien et al. |
| 5,378,848 | A | 1/1995 | Takada et al. |
| 5,389,640 | A | 2/1995 | Gerster et al. |
| 5,395,937 | A | 3/1995 | Nikolaides et al. |
| 5,444,065 | A | 8/1995 | Nikolaides et al. |
| 5,446,153 | A | 8/1995 | Lindstrom et al. |
| 5,446,160 | A | 8/1995 | Stucky et al. |
| 5,482,936 | A | 1/1996 | Lindstrom |
| 5,494,916 | A | 2/1996 | Lindstrom et al. |
| 5,500,228 | A | 3/1996 | Lawter et al. |
| 5,525,612 | A | 6/1996 | Gerster |
| 5,530,114 | A | 6/1996 | Bennett et al. |
| 5,569,450 | A | 10/1996 | Duan et al. |
| 5,571,819 | A | 11/1996 | Sabb et al. |
| 5,578,727 | A | 11/1996 | Andre et al. |
| 5,585,612 | A | 12/1996 | Harp, Jr. |
| 5,602,256 | A | 2/1997 | Andr e et al. |

(Continued)

FOREIGN PATENT DOCUMENTS

AU 2004220534 A1 9/2004

(Continued)

OTHER PUBLICATIONS

Agrawal et al (Biochem Soc Trans, Dec. 2007, 35(Pt 6): 1461-1467).*

(Continued)

*Primary Examiner* — Sean E Aeder

(57) ABSTRACT

The present invention provides methods for increasing expression of cell surface molecules of CD5$^+$ B cell lymphoma cells by contacting cells with immune response modifiers. The invention also provides methods for the treatment of CD5$^+$ B cell lymphomas, including chronic lymphocytic leukemia and small lymphocytic lymphoma, by administering immune response modifier compounds to a subject in need of such treatment. Suitable immune response modifier compounds include agonists of TLR7 and/or TLR8.

4 Claims, 11 Drawing Sheets

U.S. PATENT DOCUMENTS 5,605,899 A 2/1997 Gerster et al.
5,612,377 A 3/1997 Crooks et al.
5,627,281 A 5/1997 Nikolaides et al.
5,644,063 A 7/1997 Lindstrom et al.
5,648,516 A 7/1997 Nikolaides et al.
5,693,811 A 12/1997 Lindstrom
5,714,608 A 2/1998 Gerster
5,731,193 A 3/1998 Mori et al.
5,736,553 A 4/1998 Wick et al.
5,741,908 A 4/1998 Gerster et al.
5,741,909 A 4/1998 Gerster et al.
5,750,134 A 5/1998 Scholz et al.
5,756,747 A 5/1998 Gerster
5,776,432 A 7/1998 Schultz et al.
5,780,045 A 7/1998 McQuinn et al.
5,837,809 A 11/1998 Grandy et al.
5,840,744 A 11/1998 Borgman
5,854,257 A 12/1998 Armitage et al.
5,861,268 A 1/1999 Tang et al.
5,886,006 A 3/1999 Nikolaides et al.
5,939,047 A 8/1999 Jernberg
5,939,090 A 8/1999 Beaurline et al.
5,962,479 A 10/1999 Chen
5,962,636 A 10/1999 Bachmaier et al.
5,977,366 A 11/1999 Gerster et al.
6,028,076 A 2/2000 Hirota et al.
6,039,969 A 3/2000 Tomai et al.
6,057,371 A 5/2000 Glennon
6,069,140 A 5/2000 Sessler et al.
6,069,149 A 5/2000 Nanba et al.
6,071,949 A 6/2000 Mulshine et al.
6,077,349 A 6/2000 Kikuchi
6,083,505 A 7/2000 Miller et al.
6,110,929 A 8/2000 Gerster et al.
6,113,918 A 9/2000 Johnson et al.
6,121,323 A 9/2000 Merrill
6,123,957 A 9/2000 Jernberg
6,126,938 A 10/2000 Guy et al.
6,194,388 B1 2/2001 Krieg et al.
6,194,425 B1 2/2001 Gerster et al.
6,200,592 B1 3/2001 Tomai et al.
6,207,646 B1 3/2001 Krieg et al.
6,239,116 B1 5/2001 Krieg et al.
6,245,776 B1 6/2001 Skwierczynski et al.
6,294,271 B1 9/2001 Sumita et al.
6,303,347 B1 10/2001 Johnson et al.
6,309,623 B1 10/2001 Weers et al.
6,315,985 B1 11/2001 Wu et al.
6,323,200 B1 11/2001 Gerster et al.
6,329,381 B1 12/2001 Kurimoto et al.
6,331,539 B1 12/2001 Crooks et al.
6,339,068 B1 1/2002 Krieg et al.
6,348,462 B1 2/2002 Gerster et al.
6,365,166 B2 4/2002 Beaurline et al.
6,376,501 B1 4/2002 Isobe et al.
6,376,669 B1 4/2002 Rice et al.
6,387,383 B1 5/2002 Dow et al.
6,387,938 B1 5/2002 Mizuguchi et al.
6,406,705 B1 6/2002 Davis et al.
6,426,334 B1 7/2002 Agrawal et al.
6,440,992 B1 8/2002 Gerster et al.
6,451,485 B1 9/2002 James et al.
6,451,810 B1 9/2002 Coleman et al.
6,465,654 B2 10/2002 Gerster et al.
6,476,000 B1 11/2002 Agrawal
6,486,168 B1 11/2002 Skwierczynski et al.
6,486,186 B2 11/2002 Fowler et al.
6,511,485 B2 1/2003 Hirt et al.
6,514,985 B1 2/2003 Gerster et al.
6,518,239 B1 2/2003 Kuo et al.
6,518,265 B1 2/2003 Kato et al.
6,518,280 B2 2/2003 Gerster et al.
6,525,028 B1 2/2003 Johnson et al.
6,525,064 B1 2/2003 Dellaria et al.
6,541,485 B1 4/2003 Crooks et al.
6,545,016 B1 4/2003 Dellaria et al.
6,545,017 B1 4/2003 Dellaria et al.
6,558,951 B1 5/2003 Tomai et al.
6,573,273 B1 6/2003 Crooks et al.
6,582,957 B1 6/2003 Turner, Jr. et al.
6,610,319 B2 8/2003 Tomai et al.
6,627,638 B2 9/2003 Gerster et al.
6,627,639 B2 9/2003 Stack et al.
6,627,640 B2 9/2003 Gerster et al.
6,630,588 B2 10/2003 Rice et al.
6,638,944 B2 10/2003 Mickelson
6,649,172 B2 11/2003 Johnson
6,656,938 B2 12/2003 Crooks et al.
6,660,735 B2 12/2003 Crooks et al.
6,660,747 B2 12/2003 Crooks et al.
6,664,260 B2 12/2003 Charles et al.
6,664,264 B2 12/2003 Dellaria et al.
6,664,265 B2 12/2003 Crooks et al.
6,667,312 B2 12/2003 Bonk et al.
6,670,372 B2 12/2003 Charles et al.
6,677,334 B2 1/2004 Gerster et al.
6,677,347 B2 1/2004 Crooks et al.
6,677,348 B2 1/2004 Heppner et al.
6,677,349 B1 * 1/2004 Griesgraber .................. 514/293
6,683,088 B2 1/2004 Crooks et al.
6,696,076 B2 2/2004 Tomai et al.
6,696,465 B2 2/2004 Dellaria et al.
6,703,402 B2 3/2004 Gerster et al.
6,706,728 B2 3/2004 Hedenstrom et al.
6,716,988 B2 4/2004 Dellaria et al.
6,720,333 B2 4/2004 Dellaria et al.
6,720,334 B2 4/2004 Dellaria et al.
6,720,422 B2 4/2004 Dellaria et al.
6,743,920 B2 6/2004 Lindstrom et al.
6,756,382 B2 6/2004 Coleman et al.
6,780,873 B2 8/2004 Crooks et al.
6,784,188 B2 8/2004 Crooks et al.
6,790,961 B2 9/2004 Gerster et al.
6,797,718 B2 9/2004 Dellaria et al.
6,800,624 B2 10/2004 Crooks et al.
6,818,650 B2 11/2004 Griesgraber
6,825,350 B2 11/2004 Crooks et al.
6,841,678 B2 1/2005 Merli et al.
6,852,861 B2 2/2005 Merli et al.
6,855,217 B2 2/2005 Suzuki
6,855,350 B2 2/2005 Lu
6,878,719 B2 4/2005 Lindstrom et al.
6,888,000 B2 5/2005 Crooks et al.
6,894,060 B2 5/2005 Slade
6,894,165 B2 5/2005 Gerster et al.
6,897,221 B2 5/2005 Crooks et al.
6,900,016 B1 5/2005 Venter et al.
6,903,113 B2 6/2005 Heppner et al.
6,916,925 B1 7/2005 Rice et al.
6,921,826 B2 7/2005 Dellaria et al.
6,924,293 B2 8/2005 Lindstrom
6,943,240 B2 9/2005 Bauer et al.
6,943,255 B2 9/2005 Lindstrom et al.
6,949,649 B2 9/2005 Bonk et al.
6,953,804 B2 10/2005 Dellaria et al.
6,969,722 B2 11/2005 Heppner et al.
6,989,389 B2 1/2006 Heppner et al.
7,030,129 B2 4/2006 Miller et al.
7,030,131 B2 4/2006 Crooks et al.
7,038,053 B2 5/2006 Lindstrom et al.
7,049,439 B2 5/2006 Crooks et al.
7,078,253 B2 7/2006 Brunner et al.
7,078,523 B2 7/2006 Crooks et al.
7,091,214 B2 8/2006 Hays et al.
7,098,221 B2 8/2006 Heppner et al.
7,112,677 B2 9/2006 Griesgraber
7,115,622 B2 10/2006 Crooks et al.
7,125,890 B2 10/2006 Dellaria et al.
7,132,429 B2 11/2006 Griesgraber et al.
7,163,947 B2 1/2007 Griesgraber et al.
7,179,253 B2 2/2007 Graham et al.
7,199,131 B2 4/2007 Lindstrom
7,214,675 B2 5/2007 Griesgraber
7,220,758 B2 5/2007 Dellaria et al.
7,226,928 B2 6/2007 Mitra et al.
7,276,515 B2 10/2007 Dellaria et al.
7,288,550 B2 10/2007 Dellaria et al.

7,375,180 B2 5/2008 Gorden et al.
7,387,271 B2 6/2008 Noelle et al.
7,393,859 B2 7/2008 Coleman et al.
7,427,629 B2 9/2008 Kedl et al.
7,544,697 B2 6/2009 Hays et al.
7,598,382 B2 10/2009 Hays et al.
7,612,083 B2 11/2009 Griesgraber
7,648,997 B2 1/2010 Kshirsagar et al.
2001/0046968 A1 11/2001 Zagon et al.
2002/0016332 A1 2/2002 Slade
2002/0055517 A1 5/2002 Smith
2002/0058674 A1 5/2002 Hedenstrom et al.
2002/0107262 A1 8/2002 Lindstrom
2002/0110840 A1 8/2002 Tomai et al.
2002/0137101 A1 9/2002 Meyers
2002/0173655 A1 11/2002 Dellaria et al.
2002/0193729 A1 12/2002 Cormier et al.
2003/0022302 A1 1/2003 Lewis et al.
2003/0044429 A1 3/2003 Aderem et al.
2003/0082108 A1 5/2003 Mulshine et al.
2003/0088102 A1 5/2003 Matsubara et al.
2003/0096835 A1 5/2003 Crooks et al.
2003/0096998 A1 5/2003 Gerster et al.
2003/0130299 A1 7/2003 Crooks et al.
2003/0133733 A1 7/2003 Korhonen
2003/0133913 A1 7/2003 Tomai et al.
2003/0139364 A1 7/2003 Krieg et al.
2003/0144283 A1 7/2003 Coleman et al.
2003/0144286 A1 7/2003 Frenkel et al.
2003/0158192 A1 8/2003 Crooks et al.
2003/0161797 A1 8/2003 Miller et al.
2003/0172391 A1 9/2003 Turner et al.
2003/0185835 A1 10/2003 Braun
2003/0187016 A1 10/2003 Crooks et al.
2003/0199461 A1 10/2003 Averett et al.
2003/0199538 A1 10/2003 Skwierczynski et al.
2003/0212092 A1 11/2003 Heppner et al.
2003/0216481 A1 11/2003 Jia
2003/0232074 A1 12/2003 Lipford et al.
2003/0232763 A1 12/2003 Jia
2003/0232852 A1 12/2003 Lindstrom et al.
2004/0010007 A1 1/2004 Dellaria et al.
2004/0014779 A1 1/2004 Gorden et al.
2004/0023870 A1 2/2004 Dedera et al.
2004/0067975 A1 4/2004 Crooks et al.
2004/0072858 A1 4/2004 Charles et al.
2004/0076633 A1 4/2004 Thomsen et al.
2004/0091491 A1 5/2004 Kedl et al.
2004/0092545 A1 5/2004 Crooks et al.
2004/0097542 A1 5/2004 Crooks et al.
2004/0106638 A1 6/2004 Lindstrom
2004/0132079 A1 7/2004 Gupta et al.
2004/0132748 A1 7/2004 Isobe et al.
2004/0132766 A1 7/2004 Griesgraber
2004/0141950 A1 7/2004 Noelle et al.
2004/0147543 A1 7/2004 Hays et al.
2004/0157874 A1 8/2004 Crooks et al.
2004/0162309 A1 8/2004 Gorden et al.
2004/0167157 A1 8/2004 Masui et al.
2004/0171086 A1 9/2004 Fink et al.
2004/0175336 A1 9/2004 Egging et al.
2004/0176367 A1 9/2004 Griesgraber et al.
2004/0180919 A1 9/2004 Miller et al.
2004/0181130 A1 9/2004 Miller et al.
2004/0181211 A1 9/2004 Graham et al.
2004/0191833 A1 9/2004 Fink et al.
2004/0192585 A1 9/2004 Owens et al.
2004/0197865 A1 10/2004 Gupta et al.
2004/0202720 A1 10/2004 Wightman et al.
2004/0204436 A1 10/2004 Gerster et al.
2004/0214851 A1 10/2004 Birmachu et al.
2004/0258698 A1 12/2004 Wightman et al.
2004/0265351 A1 12/2004 Miller et al.
2005/0009858 A1 1/2005 Martinez-Colon et al.
2005/0032829 A1 2/2005 Lindstrom et al.
2005/0048072 A1 3/2005 Kedl et al.
2005/0054590 A1 3/2005 Averett
2005/0054640 A1 3/2005 Griesgraber et al.
2005/0054665 A1 3/2005 Miller et al.
2005/0059072 A1 3/2005 Birmachu et al.
2005/0070460 A1 3/2005 Hammerbeck et al.
2005/0085500 A1 4/2005 Gutman et al.
2005/0096259 A1 5/2005 Tomai et al.
2005/0119273 A1 6/2005 Lipford et al.
2005/0136065 A1 6/2005 Valiante
2005/0148620 A1 7/2005 Crooks et al.
2005/0158325 A1 7/2005 Hammerbeck et al.
2005/0165236 A1 7/2005 Colombo et al.
2005/0171072 A1 8/2005 Tomai et al.
2005/0226878 A1 10/2005 Tomai et al.
2005/0234088 A1 10/2005 Griesgraber
2005/0239733 A1 10/2005 Jurk et al.
2005/0239735 A1 10/2005 Miller et al.
2005/0245562 A1 11/2005 Garcia-Echeverria et al.
2005/0267145 A1 12/2005 Merrill et al.
2005/0281813 A1 12/2005 Dedera et al.
2006/0009482 A1 1/2006 Tomai et al.
2006/0100229 A1 5/2006 Hays et al.
2006/0106052 A1 5/2006 Crooks et al.
2006/0188913 A1 8/2006 Krieg et al.
2007/0060754 A1 3/2007 Lindstrom et al.
2007/0066639 A1 3/2007 Kshirsagar et al.
2007/0072893 A1 3/2007 Krepski et al.
2007/0099901 A1 5/2007 Krepski et al.
2007/0155767 A1 7/2007 Radmer et al.
2007/0166384 A1 7/2007 Zarraga
2007/0167476 A1 7/2007 Kshirsagar et al.
2007/0208052 A1 9/2007 Prince et al.
2007/0213356 A1 9/2007 Merrill et al.
2007/0219196 A1 9/2007 Krepski et al.
2007/0219228 A1 9/2007 Niwas et al.
2007/0259881 A1 11/2007 Dellaria et al.
2007/0259907 A1 11/2007 Prince
2007/0287725 A1 12/2007 Miser et al.
2007/0292456 A1 12/2007 Hammerbeck et al.
2008/0015184 A1 1/2008 Kshirsagar et al.
2008/0070907 A1 3/2008 Griesgraber et al.
2008/0085895 A1 4/2008 Griesgraber et al.
2008/0114019 A1 5/2008 Kshirsagar et al.
2008/0119508 A1 5/2008 Slade et al.
2008/0207674 A1 8/2008 Stoesz et al.
2008/0269192 A1 10/2008 Griesgraber et al.
2008/0306252 A1 12/2008 Crooks et al.
2008/0312434 A1 12/2008 Lindstrom et al.
2008/0318998 A1 12/2008 Prince et al.
2009/0005371 A1 1/2009 Rice et al.
2009/0018122 A1 1/2009 Lindstrom et al.
2009/0023722 A1 1/2009 Coleman et al.
2009/0029988 A1 1/2009 Kshirsagar et al.
2009/0030030 A1 1/2009 Bonk et al.
2009/0030031 A1 1/2009 Kshirsagar et al.
2009/0042925 A1 2/2009 Kshirsagar et al.
2009/0062272 A1 3/2009 Bonk et al.
2009/0062328 A1 3/2009 Kshirsagar et al.
2009/0069299 A1 3/2009 Merrill et al.
2009/0069314 A1 3/2009 Kshirsagar et al.
2009/0075980 A1 3/2009 Hays et al.
2009/0099161 A1 4/2009 Rice et al.
2009/0105295 A1 4/2009 Kshirsagar et al.
2009/0124611 A1 5/2009 Hays et al.
2009/0163532 A1 6/2009 Perman et al.
2009/0163533 A1 6/2009 Hays et al.
2009/0176821 A1 7/2009 Kshirsagar et al.
2009/0240055 A1 9/2009 Krepski et al.
2009/0253695 A1 10/2009 Kshirsagar et al.
2009/0270443 A1 10/2009 Stoermer et al.
2009/0318435 A1 12/2009 Hays et al.
2010/0113565 A1 5/2010 Gorden et al.
2010/0240693 A1 9/2010 Lundquist, Jr. et al.

FOREIGN PATENT DOCUMENTS

AU 2004229478 A1 10/2004
AU 2004264336 A1 2/2005
AU 2004268625 A1 3/2005
AU 2002239547 B2 11/2006
CA 2044087 A1 12/1991
CA 2158996 A1 10/1994
CN 1354663 A 6/2002

| | | | |
|---|---|---|---|
| EP | 0 145 340 | A2 | 6/1985 |
| EP | 0 223 420 | A1 | 5/1987 |
| EP | 0 310 950 | A1 | 4/1989 |
| EP | 0 385 630 | A2 | 9/1990 |
| EP | 0 389 302 | A1 | 9/1990 |
| EP | 0 394 026 | A1 | 10/1990 |
| EP | 0 425 306 | A2 | 5/1991 |
| EP | 0 510 260 | A2 | 10/1992 |
| EP | 0 556 008 | A1 | 8/1993 |
| EP | 0 645 389 | A1 | 3/1995 |
| EP | 0 778 277 | A1 | 6/1997 |
| EP | 0 894 797 | A1 | 2/1999 |
| EP | 1 082 960 | A2 | 3/2001 |
| EP | 1 097 709 | A2 | 5/2001 |
| EP | 1 104 764 | A1 | 6/2001 |
| EP | 1 145 340 | A2 | 10/2001 |
| EP | 1 256 582 | A1 | 11/2002 |
| EP | 1 341 791 | A2 | 9/2003 |
| EP | 1 495 758 | A2 | 1/2005 |
| HU | 34479 | A2 | 3/1985 |
| HU | 210051 | A2 | 6/1991 |
| HU | 218950 | A2 | 9/1995 |
| IL | 73534 | A | 12/1990 |
| JP | 53050197 | A | 5/1978 |
| JP | 63010787 | A | 1/1988 |
| JP | 1180156 | A | 7/1989 |
| JP | 4066571 | A | 3/1992 |
| JP | 4327587 | A | 11/1992 |
| JP | 5286973 | A | 11/1993 |
| JP | 9208584 | A | 8/1997 |
| JP | 11222432 | A | 8/1999 |
| JP | 2000247884 | A | 9/2000 |
| NZ | 545412 | A | 12/2008 |
| RU | 2076105 | C1 | 3/1997 |
| RU | 2127273 | C1 | 3/1999 |
| RU | 2221798 | C2 | 1/2004 |
| WO | WO-91/06682 | A1 | 5/1991 |
| WO | WO-92/06093 | A1 | 4/1992 |
| WO | WO-92/15581 | A1 | 9/1992 |
| WO | WO-92/15582 | A1 | 9/1992 |
| WO | WO-93/05042 | A1 | 3/1993 |
| WO | WO-93/09119 | A1 | 5/1993 |
| WO | WO-93/20847 | A1 | 10/1993 |
| WO | WO-94/10171 | A1 | 5/1994 |
| WO | WO-95/02597 | A1 | 1/1995 |
| WO | WO-95/02598 | A1 | 1/1995 |
| WO | WO-96/11199 | A1 | 4/1996 |
| WO | WO-96/21663 | A1 | 7/1996 |
| WO | WO-97/48703 | A1 | 12/1997 |
| WO | WO-97/48704 | A1 | 12/1997 |
| WO | WO-98/17279 | A1 | 4/1998 |
| WO | WO-98/30562 | A1 | 7/1998 |
| WO | WO-98/48805 | A1 | 11/1998 |
| WO | WO-98/50547 | A2 | 11/1998 |
| WO | WO-98/54226 | A1 | 12/1998 |
| WO | WO-99/18105 | A1 | 4/1999 |
| WO | WO-99/29693 | A1 | 6/1999 |
| WO | WO-00/06577 | A1 | 2/2000 |
| WO | WO-00/09506 | A1 | 2/2000 |
| WO | WO-00/19987 | A1 | 4/2000 |
| WO | WO-00/40228 | A2 | 7/2000 |
| WO | WO-00/47719 | A2 | 8/2000 |
| WO | WO-00/75304 | A1 | 12/2000 |
| WO | WO-00/76505 | A1 | 12/2000 |
| WO | WO-00/76518 | A1 | 12/2000 |
| WO | WO-00/76519 | A1 | 12/2000 |
| WO | WO-01/34709 | A1 | 5/2001 |
| WO | WO-01/51486 | A2 | 7/2001 |
| WO | WO-01/55439 | A1 | 8/2001 |
| WO | WO-01/58900 | A1 | 8/2001 |
| WO | WO-01/74343 | A2 | 10/2001 |
| WO | WO-01/74821 | A1 | 10/2001 |
| WO | WO-02/07725 | A1 | 1/2002 |
| WO | WO-02/22809 | A2 | 3/2002 |
| WO | WO-02/24225 | A1 | 3/2002 |
| WO | WO-02/36592 | A1 | 5/2002 |
| WO | WO-02/46188 | A2 | 6/2002 |
| WO | WO-02/46189 | A2 | 6/2002 |
| WO | WO-02/46190 | A2 | 6/2002 |
| WO | WO-02/46191 | A2 | 6/2002 |
| WO | WO-02/46192 | A2 | 6/2002 |
| WO | WO-02/46193 | A2 | 6/2002 |
| WO | WO-02/46194 | A2 | 6/2002 |
| WO | WO-02/46749 | A2 | 6/2002 |
| WO | WO-02/085905 | A1 | 10/2002 |
| WO | WO-02/102377 | A1 | 12/2002 |
| WO | WO-03/008421 | A1 | 1/2003 |
| WO | WO-03/009852 | A1 | 2/2003 |
| WO | WO-03/020889 | A2 | 3/2003 |
| WO | WO-03/043572 | A2 | 5/2003 |
| WO | WO-03/045391 | A1 | 6/2003 |
| WO | WO-03/045494 | A2 | 6/2003 |
| WO | WO-03/045929 | A1 | 6/2003 |
| WO | WO-03/050117 | A1 | 6/2003 |
| WO | WO-03/050118 | A1 | 6/2003 |
| WO | WO-03/050119 | A2 | 6/2003 |
| WO | WO-03/050121 | A1 | 6/2003 |
| WO | WO-03/077944 | A1 | 9/2003 |
| WO | WO-03/080114 | A2 | 10/2003 |
| WO | WO-03/086280 | A2 | 10/2003 |
| WO | WO-03/086350 | A1 | 10/2003 |
| WO | WO-03/089602 | A2 | 10/2003 |
| WO | WO-03/097641 | A2 | 11/2003 |
| WO | WO-03/101949 | A2 | 12/2003 |
| WO | WO-03/103584 | A2 | 12/2003 |
| WO | WO-2004/009593 | A1 | 1/2004 |
| WO | WO-2004/028539 | A2 | 4/2004 |
| WO | WO-2004/041285 | A1 | 5/2004 |
| WO | WO-2004/043913 | A2 | 5/2004 |
| WO | WO-2004/053057 | A2 | 6/2004 |
| WO | WO-2004/053452 | A2 | 6/2004 |
| WO | WO-2004/058759 | A1 | 7/2004 |
| WO | WO-2004/071459 | A2 | 8/2004 |
| WO | WO-2004/075865 | A2 | 9/2004 |
| WO | WO-2004/080398 | A2 | 9/2004 |
| WO | WO-2004/091500 | A2 | 10/2004 |
| WO | WO-2004/096144 | A2 | 11/2004 |
| WO | WO-2004/110991 | A2 | 12/2004 |
| WO | WO-2004/110992 | A2 | 12/2004 |
| WO | WO-2005/003064 | A2 | 1/2005 |
| WO | WO-2005/003065 | A2 | 1/2005 |
| WO | WO-2005/016273 | A2 | 2/2005 |
| WO | WO-2005/016275 | A2 | 2/2005 |
| WO | WO-2005/018551 | A2 | 3/2005 |
| WO | WO-2005/018555 | A2 | 3/2005 |
| WO | WO-2005/018556 | A2 | 3/2005 |
| WO | WO-2005/020999 | A1 | 3/2005 |
| WO | WO-2005/023190 | A2 | 3/2005 |
| WO | WO-2005/025614 | A3 | 3/2005 |
| WO | WO-2005/029037 | A2 | 3/2005 |
| WO | WO-2005/032484 | A3 | 4/2005 |
| WO | WO-2005/041891 | A2 | 5/2005 |
| WO | WO-2005/048933 | A2 | 6/2005 |
| WO | WO-2005/048945 | A2 | 6/2005 |
| WO | WO-2005/049076 | A1 | 6/2005 |
| WO | WO-2005/051317 | A2 | 6/2005 |
| WO | WO-2005/051324 | A2 | 6/2005 |
| WO | WO-2005/054237 | A1 | 6/2005 |
| WO | WO-2005/054238 | A1 | 6/2005 |
| WO | WO-2005/065678 | A1 | 7/2005 |
| WO | WO-2005/066169 | A2 | 7/2005 |
| WO | WO-2005/066170 | A1 | 7/2005 |
| WO | WO-2005/066172 | A1 | 7/2005 |
| WO | WO-2005/067500 | A2 | 7/2005 |
| WO | WO-2005/076783 | A2 | 8/2005 |
| WO | WO-2005/079195 | A2 | 9/2005 |
| WO | WO-2005/094531 | A2 | 10/2005 |
| WO | WO-2005/110013 | A2 | 11/2005 |
| WO | WO-2005/123079 | A2 | 12/2005 |
| WO | WO-2005/123080 | A2 | 12/2005 |
| WO | WO-2006/004737 | A2 | 1/2006 |
| WO | WO-2006/009826 | A1 | 1/2006 |
| WO | WO-2006/009832 | A1 | 1/2006 |
| WO | WO-2006/026760 | A2 | 3/2006 |
| WO | WO-2006/028451 | A1 | 3/2006 |
| WO | WO-2006/028545 | A2 | 3/2006 |
| WO | WO-2006/028962 | A2 | 3/2006 |
| WO | WO-2006/029115 | A2 | 3/2006 |

| | | | |
|---|---|---|---|
| WO | WO-2006/031878 | A2 | 3/2006 |
| WO | WO-2006/038923 | A2 | 4/2006 |
| WO | WO-2006/063072 | A2 | 6/2006 |
| WO | WO-2006/063152 | A2 | 6/2006 |
| WO | WO-2006/065280 | A2 | 6/2006 |
| WO | WO-2006/073940 | A2 | 7/2006 |
| WO | WO-2006/074003 | A2 | 7/2006 |
| WO | WO-2006/074045 | A2 | 7/2006 |
| WO | WO-2006/083440 | A2 | 8/2006 |
| WO | WO-2006/084251 | A2 | 8/2006 |
| WO | WO-2006/086449 | A2 | 8/2006 |
| WO | WO-2006/086633 | A2 | 8/2006 |
| WO | WO-2006/086634 | A2 | 8/2006 |
| WO | WO-2006/091394 | A2 | 8/2006 |
| WO | WO-2006/091567 | A2 | 8/2006 |
| WO | WO-2006/091568 | A2 | 8/2006 |
| WO | WO-2006/091647 | A2 | 8/2006 |
| WO | WO-2006/093514 | A2 | 9/2006 |
| WO | WO-2006/098852 | A2 | 9/2006 |
| WO | WO-2006/107753 | A2 | 10/2006 |
| WO | WO-2006/107771 | A2 | 10/2006 |
| WO | WO-2006/107851 | A1 | 10/2006 |
| WO | WO-2006/107853 | A2 | 10/2006 |
| WO | WO-2006/121528 | A2 | 11/2006 |
| WO | WO-2006/122806 | A2 | 11/2006 |
| WO | WO-2007/028129 | A1 | 3/2007 |
| WO | WO-2007/030775 | A2 | 3/2007 |
| WO | WO-2007/030777 | A2 | 3/2007 |
| WO | WO-2007/035935 | A1 | 3/2007 |
| WO | WO-2007/056112 | A2 | 5/2007 |
| WO | WO-2007/062043 | A1 | 5/2007 |
| WO | WO-2007/075468 | A1 | 7/2007 |
| WO | WO-2007/079086 | A1 | 7/2007 |
| WO | WO-2007/079146 | A1 | 7/2007 |
| WO | WO-2007/079169 | A2 | 7/2007 |
| WO | WO-2007/079171 | A2 | 7/2007 |
| WO | WO-2007/079202 | A2 | 7/2007 |
| WO | WO-2007/079203 | A2 | 7/2007 |
| WO | WO-2007/092641 | A2 | 8/2007 |
| WO | WO-2007/106852 | A2 | 9/2007 |
| WO | WO-2007/106854 | A2 | 9/2007 |
| WO | WO-2007/120121 | A2 | 10/2007 |
| WO | WO-2007/143526 | A2 | 12/2007 |
| WO | WO-2008/008432 | A2 | 1/2008 |
| WO | WO-2008/030511 | A2 | 3/2008 |
| WO | WO-2008/036312 | A1 | 3/2008 |
| WO | WO-2008/045543 | A1 | 4/2008 |

OTHER PUBLICATIONS

Levy et al (Blood, Aug. 2006, 108(4): 1284-1290).*

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Buschle et al., Interferon gamma inhibits apoptotic cell death in B cell chronic lymphocytic leukemia. J Exp Med. Jan. 1, 1993;177(1):213-8.

Edwards et al., Toll-like receptor expression in murine DC subsets: lack of TLR7 expression by CD8 alpha+ DC correlates with unresponsiveness to imidazoquinolines. Eur J Immunol. Apr. 2003,33(4):827-33.

Hemmi et al., Small anti-viral compounds activate immune cells via the TLR7 MyD88-dependent signaling pathway. Nat Immunol. Feb. 2002;3(2):196-200. Epub Jan. 22, 2002.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract Only.

Spaner et al., A phase I/II trial of TLR -7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Tomic et al., Sensitization of IL-2 Signaling through TLR-7 Enhances B Lymphoma Cell Immunogenicity. J Immunol. 2006;176:3830-39.

Supplementary European Search Report for EP 04783053.4 mailed Jun. 13, 2008.

International Search Report and Written Opinion for PCT/US2004/028688 mailed Apr. 14, 2006.

International Preliminary Report on Patentability for PCT/US2004/028688 mailed May 26, 2006.

Office Communication mailed Apr. 30, 2007 for U.S. Appl. No. 10/933,594.

Office Communication mailed Jan. 15, 2008 for U.S. Appl. No. 10/933,594.

[No Author Listed] "Comparative Tests." Filed Apr. 8, 2005 during prosecution for EP 00938205.2, EP 00950215.4 and EP 00938211.0 in the name of 3M Innovative Properties Co.

[No Author Listed] Chemical Abstracts. 1964;61(1):6060g.

[No Author Listed] Encyclopedia of Pharmaceutical Technology. 2nd Ed. Marcel Dekker, Inc. 2002:856-60.

Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.

Akira et al., Recognition of pathogen-associated molecular patterns by TLR family. Immunol Lett. 2003;85:85-95.

Akira et al., Toll-like receptors: critical proteins linking innate and acquired immunity. Nature Immunol. 2001;2(8):675-80.

Alexopoulou et al., Recognition of double-stranded RNA and activation of NF-kappaB by Toll-like receptor 3. Nature. Oct. 18, 2004;413(6857):732-8.

Assuma et al., IL-1 and TNF Antagonists Inhibit the Inflammatory Response and Bone Loss in Experimental Periodontitis. J Immunol. 2000;160:403-09.

Au et al., Virus-mediated induction of interferon A gene requires cooperation between multiple binding factors in the interferon alpha promoter region. J Biol Chem. Nov. 15, 1993;268(32):24032-40.

Auerbach et al., Erythema nodosum following a jellyfish sting. J Emerg Med. Nov.-Dec. 1987;5(6):487-91.

Auwers, [Uber die Isomerie-Verhaltnisse in der Pyrazol-Reihe. Berichte. VI.] 1926;601-607. German.

Bachman et al., Synthesis of substituted quinolylamines. Derivatives of 4-amino-7-chloroquinoline. J Org Chem. 1950;15(6):1278-84.

Baffis et al., Use of interferon for prevention of hepatocellular carcinoma in cirrhotic patients with hepatitis B or hepatitis C virus infection. Ann Intern Med. Nov. 2, 1999;131(9):696-701.

Baker et al., Oral infection with Porphyromonas gingivalis and induced alveolar bone loss in immunocompetent and severe combined immunodeficient mice. Arch Oral Biol. Dec. 1994;39(12):1035-40.

Baldwin et al., Amino Acid Synthesis *via* Ring Opening of N-Sulphonyl Aziridine-2-Carboxylate Esters with Organometallic Reagents. Tetrahedron. 1993;49:6309-30.

Baranov et al., Imidazo[4-5c]quinolines. In Chemical Abstracts. 1976;85:637. Abstract 94362z.

Bártová et al., Th1 and Th2 cytokine profile in patients with early onset periodontitis and their healthy siblings. Mediators Inflamm. 2000;9(2):115-20.

Beck et al., Dental Infections and Atherosclerosis. Am Heart J. 1999;13:528-33.

Beckett et al., Configurational Studies in Synthetic Analgesics: the Synthesis of (-)-Methadone from D-(-)-Alanine. J Chem Soc. 1957;1:858-61.

Beilman et al., Experimental brown spider bite in the guinea pig: Results of treatment with dapsone or hyperbaric oxygen. J Wilderness Medicine. 1994;5:287-94.

Belikov, Abbreviated Guide to Synthetic and Natural Medications. Pharmaceutical Chemistry. Higher School. 1993;1:43-47. Russian.

Beltrami et al., Some Methylhydrazonium Salts; An Improved Synthesis of Tetramethylhydrazine. J Am Chem Soc. 1956;78:2467-68.

Berenyi et al., Ring transformation of condensed dihyrdo-as-triazines. J Heterocyclic Chem. 1981;18:1537-40.

Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.
Bertino et al., Principles of Cancer Therapy. Cecil Textbook of Medicine. Goldman et al., eds. 21th Ed. W.B. Saunders Company. 2000:1:1060-74.
Beutler et al., Tumor necrosis factor in the pathogenesis of infectious diseases. Crit Care Med. Oct. 1993;21(10 Suppl):S423-35.
Beutner et al., Therapeutic response of basal cell carcinoma to the immune response modifier imiquimod 5% cream. J Am Acad Dermatol. Dec. 1999;41(6):1002-7.
Beutner et al., Treatment of genital warts with an immune-response modifier (imiquimod). J Am Acad Dermatol. Feb. 1998;38(2 Pt 1):230-9.
Binder, Acute arthropod envenomation. Incidence, clinical features and management. Med Toxicol Adverse Drug Exp. May-Jun. 1989;4(3):163-73.
Bishop et al., Molecular mechanisms of B lymphocyte activation by the immune response modifier R-848. J Immunol. Nov. 15, 2000;165(10):5552-7.
Bitterman-Deutsch et al., [Brown spider bite]. Harefuah. Sep. 1990;119(5-6):137-9. Hebrew.
Booth et al., Dapsone suppresses integrin-mediated neutrophil adherence function. J Invest Dermatol. Feb. 1992;98(2):135-40.
Borkan et al., An outbreak of venomous spider bites in a citrus grove. Am J Trop Med Hyg. Mar. 1995;52(3):228-30.
Brants, The Distribution of Tobacco Mosaic Virus (TMV) in Excised Tomato Roots Cultivated in Vitro. Tijdschr Plantenziekten, 1962;68:198-207.
Brassard et al., Interferon-α as an immunotherapeutic protein. J Leukoc Biol. Apr. 2002;71(4):565-81.
Breathnach, Azelaic acid: potential as a general antitumoural agent. Med Hypotheses. Mar. 1999;52(3):221-6.
Brennan et al., Automated bioassay of interferons in microtest plates. Biotechniques. Jun./Jul. 1983(1):78-82.
Broughton, Management of the brown recluse spider bite to the glans penis. Mil Med. Oct. 1996;161(10):627-9.
Buckle et al., 4-hydroxy-3-nitro-2-quinolones and related compounds as inhibitors of allergic reactions. J Med Chem. Jul. 1975;18(7):726-32.
Buisson et al., Preparation and use of (*S*)-*O*-acetyllactyl chloride (Mosandl's reagent) as a chiral derivatizing agent. Tetrahedron Assym. 1999;10:2997-3002.
Bulut et al., Cooperation of Toll-like receptor 2 and 6 for cellular activation by soluble tuberculosis factor and *Borrelia burgdorferi* outer surface protein A lipoprotein: role of Toll-interacting protein and IL-1 receptor signaling molecules in Toll-like receptor 2 signaling. J Immunol. Jul. 15, 2001;167(2):987-94.
Burleson, Chapter 14. Influenza Virus Host Resistance Model for Assessment of Immunostimulation, and Antiviral Compounds. Methods in Immunology. 1995;2:181-202.
Cai et al., Evaluation of trifluoroacetic acid as an ion-pair reagent in the separation of small ionizable molecules by reversed-phase liquid chromatography. Analytica Chmica Acta. 1999;399:249-258.
Cantell et al., IFN-γ Enhances Production of IFN-α in Human Macrophages but Not in Monocytes. J Interferon and Cytokine Res. 1996;16:461-63.
Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.
Carrigan et al., Synthesis and in vitro pharmacology of substituted quinoline-2,4-dicarboxylic acids as inhibitors of vesicular glutamate transport. J Med Chem. May 23, 2002;45(11):2260-76.
Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.
Cheson et al., National Cancer Institute-sponsored Working Group guidelines for chronic lymphocytic leukemia: revised guidelines for diagnosis and treatment. Blood. Jun. 15, 1996;87(12):4990-7.
Chollet et al., Development of a topically active imiquimod formulation. Pharm Dev Technol. Jan. 1999;4(1):35-43.
Chuang et al., Toll-like receptor 9 mediates CpG-DNA signaling. J Leukoc Biol. Mar. 2002;71(3):538-44.
Claisen, [Uber α-Methyl-isoxazol.] Berichte. 1909;42:59-69. German.
Cohen et al., Cytokine function: a study in biologic diversity. Am J Clin Pathol. May 1996;105(5):589-98.
Cole et al., Brown recluse spider envenomation of the eyelid: an animal model. Ophthal Plast Reconstr Surg. Sep. 1995;11(3):153-64.
Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.
Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.
Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.
Davis, Current therapy for chronic hepatitis C. Gastroenterology. Feb. 2000;118(2 Suppl 1):S104-14.
Davis et al., Heterocyclic Syntheses with Malonyl Chloride. Part VI. 3-Substituted Pyridine Derivatives from α-Methylene-nitriles. J Chem Soc. 1962:3638-44.
Davis et al., Self-administered topical imiquimod treatment of vulvar intraepithelial neoplasia. A report of four cases. J Reprod Med. Aug. 2000;45(8):619-23.
De et al., Structure-activity relationships for antiplasmodial activity among 7-substituted 4-aminoquinolines. J Med Chem. Dec. 3, 1998;41(25):4918-26.
Debol et al., Anti-inflammatory action of dapsone: inhibition of neutrophil adherence is associated with inhibition of chemoattractant-induced signal transduction. J Leukoc Biol. Dec. 1997;62(6):827-36.
De Clerq, Synthetic interferon inducers. Top Curr Chem. 1974;52:173-208.
Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.
Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.
Delgado, Textbook of Organic Medicinal and Pharmaceutical Chemistry, Ninth Edition, Remers, ed., 1991:30-1.
Denzel et al. Imidazo [4,5-c]- and [4,5-b]pyridines. J. Heterocyclic Chem. 1977;14:813-821.
Diaz-Arrastia et al., Clinical and molecular responses in high-grade intraepithelial neoplasia treated with topical imiquimod 5%. Clin Cancer Res. Oct. 2001;7(10):3031-3.
Di Carlo et al., Neutrophils in anti-cancer immunological strategies: old players in new games. J Hematother Stem Cell Res. Dec. 2001;10(6):739-48.
Dicken et al., Reactions at High Pressures. [3 + 2] Dipolar Cycloaddition of Nitrones with Vinyl Ethers. J Org Chem. 1982;47:2047-51.
Dockrell et al., Imiquimod and resiquimod as novel immunomodulators. J Antimicrob Chemother. Dec. 2001;48(6):751-5.
Dorwald, "Preface." Side Reactions in Organic Synthesis. A Guide to Successful Synthesis Design. Wiley-VCH. 2005: IX.
Douglas, Introduction to Viral Diseases. In: Cecil Textbook of Medicine. Bennet et al., eds. 20th Ed. W.B. Saunders Company. 1996:2:1739-47.
Doyle et al, Toll-like receptor 3 mediates a more potent antiviral response than Toll-like receptor 4. J Immunol. Apr. 1, 2003;170(7):3565-71.
Drexler et al., Bryostatin 1 induces differentiation of B-chronic lymphocytic leukemia cells. Blood. Oct. 1989;74(5):1747-57.
Dzionek et al. BDCA-2, BDCA-3, and BDCA-4: three markers for distinct subsets of dendritic cells in human peripheral blood. J Immunol. Dec. 1, 2000;165(11):6037-46.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.
Fecci et al., The history, evolution, and clinical use of dendritic cell-based immunization strategies in the therapy of brain tumors. J Neurooncol. Aug.-Sep. 2003;64(1-2):161-76.
Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.
Flo et al., Involvement of toll-like receptor (TLR) 2 and TLR4 in cell activation by mannuronic acid polymers. J Biol Chem. Sep. 20, 2002;277(38):35489-95. Epub Jun. 27, 2002.
Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.
Frankel et al., The Preparation of N-Disubstituted Formamides. Tetrahedron Lett. 1959;7:5-7.
Frantz et al., To114 (TLR4) expression in cardiac myocytes in normal and failing myocardium. J Clin Invest. Aug. 1999;104(3):271-80.
Fu et al., Regioselective Catalytic Hydrogenation of Polycyclic Aromatic Hydocarbons under Mild conditions. J Org Chem. 1980;45:2979-803.
Fuchsberger et al., Priming Interferon-a 1 or Interferon-a 2 Enhances the Production of Both Subtypes Simultaneously. J Interferon and Cytokine Res. 1995;15:637-39.
Galose, Dapsone (diaminodiphenylsulphone DDS). Clinical Toxicology Review. 1999:21(9). 3 pages.
Gendron, *Loxosceles ignali* Envenomation. Am J Emerg Med. Jan. 1980;8(1):51-4.
Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.
Giannini et al., Influence of the Mucosal Epithelium Microenvironment on Langerhans Cells: Implications for the Development of Squamous Intraepithelial Lesions of the Cervix. Int J Cancer. 2002;97:654-59.
Gibson et al., Cellular requirements for cytokine production in response to the immunomodulators imiquimod and S-27609. J Interferon Cytokine Res. Jun. 1995;15(6):537-45.
Gibson et at., Plasmacytoid dendritic cells produce cytokines and mature in response to the TLR7 agonists, imiquimod and resiquimod. Cell Immunol. Jul.-Aug. 2002;218(1-2):74-86.
Gitelson et at., Chronic lymphocytic leukemia-reactive T cells during disease progression and after autologous tumor cell vaccines. Clin Cancer Res. May 2003;9(5):1656-65.
Gomez et al., Intradermal anti-loxosceles Fab fragments attenuate dermonecrotic arachnidism. Acad Emerg Med. 1999;6:1195-202.
Gorden et at, Synthetic TLR agonists reveal functional differences between human TLR7 and TLR8. J Immunol. Feb. 1, 2005;174(3):1259-68.
Gordon, Pattern recognition receptors: doubling up for the innate immune response. Cell. Dec. 27, 2002;111(7):927-30.
Gunning et al., Chemoprevention by lipoxygenase and leukotriene pathway inhibitors of vinyl carbamate-induced lung tumors in mice. Cancer Res. Aug. 1, 2002;62(15):4199-201.
Gürsel et al., Differential and competitive activation of human immune cells by distinct classes of CpG oligodeoxynucleotide. J Leukoc Biol. May 2002;71(5):813-20.
Hart, Napthyridines Hydroxynaphthyridies, Journal of Chemical Society, 1956;Part III:212-4.
Hartmann et al., Rational design of new CpG oligonucleotides that combine B cell activation with high IFN-alpha induction in plasmacytoid dendritic cells. Eur J Immunol. Jun. 2003;33(6):1633-41.
Hayashi Toll-like receptors stimulate human neutrophil function. Blood. Oct. 1, 2003;102(7):2660-69. Epub Jun. 26, 2003.
Hayes et al., Regulation of Interferon Production by Human Monocytes: Requirements for Priming for Lipopolysaccharide-Induced Production. J Leukocyte Biol. 1991;50:176-81.
Heil et al., Species-specific recognition of single-stranded RNA via toll-like receptor 7 and 8. Science. Mar. 5, 2004;303(5663):1526-9. Epub Feb. 19, 2004.
Heil et al., Synthetic immunostimulatory compounds activate immune cells via TLR7 and TLR8. 33th Annual Meeting of the Deutsche Gessellschaft Mr Immunologie, Marburg 2002. Abstract C.6.
Hobbs et al., Comparison of hyperbaric oxygen and dapsone therapy for loxosceles envenomation. Aced Emerg Med. Aug. 1996;3(8):758-61.
Hoffman et al., Conformational requirements for histamine H2-receptor inhibitors: a structure-activity study of phenylene analogues related to cimetidine and tiotidine. J Med Chem. Feb. 1983;26(2):140-4.
Hofmanová et al., Lipoxygenase inhibitors induce arrest of tumor cells in S-phase of the cell cycle. Neoplasma. 2002;49(6):362-7.
Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.
Horng et al., The adaptor molecule TIRAP provides signaling specificity for Toll-like receptors. Nature. Nov. 21, 2002;420(6913):329-33.
Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.
Houben-Weyl, Quinoline and Isoquinoline. Methoden der Organischen Chemie. 1980:271-79. German.
Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.
Huppatz, Systemic fungicides. The synthesis of certain pyrazole analogues of carboxin. Aust J Chem. 1983;36:135-47.
Iino et al., Treatment of Chronic Hepatitis C With High-Dose Interferon α-2b. Multicenter Study. Dig Dis Sci. 1993;38(4):612-18.
Ito et al., Interferon-alpha and interleukin-12 are induced differentially by Toll-like receptor 7 ligands in human blood dendritic cell subsets. J Exp Med. Jun. 3, 2002;195(11):1507-12.
Iwashita et al., Syntheses of Isoretronecanol and Lupinine. J Org Chem. 1982;47:230-33.
Izumi et al., 1H-Imidazo[4,5-c]quinoline derivatives as novel potent TNF-alpha suppressors: synthesis and structure-activity relationship of 1-, 2-and 4-substituted 1 H-imidazo[4,5-c]quinolines or 1H-imidazo[4,5-c]pyridines. Bioorg Med Chem. Jun. 12, 2003;11(12):2541-50.
Jacobs, Chapter 1. The Synthesis of Acetylenes. In: Organic Reactions. New York: Wiley & Sons, Inc., 1949. vol. 5. 1-78.
Jahnsen et al., Extensive recruitment of IL-3Rαhigh dendritic-cell precursors to allergic nasal mucosa during allergen challenge. Immunology Lett. 1999;69(1):123. Abstract #32.2.
Jain et al., Chemical and pharmacological investigations of some omega-substituted alkylamino-3-aminopyridines. J Med Chem. Jan. 1968;11(1):87-92.
Jurk et al. Human TLR7 and TLR8 independently confer responsiveness to the antiviral compound R-848. Nat Immunol. Jun. 2002;3(6):499.
Juweid, Radioimmunotherapy of B-Cell Non-Hodgkin's Lymphoma: From Clinical Trials to Clinical Practice. J Nuclear Med. 2002;43(11):1507-29.
Katritsky et al., Comprehensive Heterocyclic Chemistry: The Structure, Reactions, Synthesis and Uses of Heterocyclic Compounds. 1984;2:586-587.
Keating et al., Long-term follow-up of patients with chronic lymphocytic leukemia treated with fludarabine as a single agent. Blood. Jun. 1, 1993;81(11):2878-84.
Kerkmann et al., Activation with CpG-A and CpG-B oligonucleotides reveals two distinct regulatory pathways of type I IFN synthesis in human plasmacytoid dendritic cells. J Immunol. May 1, 2003;170(9):4465-74.

Klausen et al., Two complementary methods of assessing periodontal bone level in rats. Scand J Dent Res. Dec. 1989;97(6):494-9.
Klinman, Immunotherapeutic uses of CpG oligodeoxynucleotides. Nat Rev Immunol. Apr. 2004;4(4):249-58.
Kloek et al., An improved method for the synthesis of stabilized primary enamines and imines. J Org Chem. 1978;43:1460-62.
Kloetzel, Reactions of nitroparaffins. I. Synthesis and reduction of some ò -nitrokenes. J Am Chem Soc. 1947;69:2271-2275.
Kornman, Host modulation as a therapeutic strategy in the treatment of periodontal disease. Clin Infect Dis. Mar. 1999 ;28(3):520-6.
Kourafalos et al., Synthesis of 7-aminopyrazolo[3,4-c]pyridine as a probe for the preparation of compounds of pharmacological interest. Heterocycles. 2002;57(12):2335-2343.
Krause et at., Autoimmune aspects of cytokine and anticytokine therapies. Am J Med. Oct. 1, 2003;115(5):390-7.
Krenitsky et al., Imidazo[4,5-c]pyridines (3-deazapurines) and their nucleosides as immunosuppressive and anti-inflammatory agents. J Med Chem. Jan. 1986;29(1):138-43.
Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.
Lall et al., Serine and threonine beta-lactones: a new class of hepatitis A virus 3C cysteine proteinase inhibitors. J Org Chem. Mar. 8, 2002;67(5):1536-47.
Lee et al., p38 mitogen-activated protein kinase inhibitors—mechanisms and therapeutic potentials. Pharmacol Ther. 1999;82:389-97.
Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.
Lehner et al., The role of γō cells and β-chemokines in mucosal protection against SIV infection. Immunology Lett. 1999;69:25-192. Abstract 2.1.
Leynadier et al., Allergic reactions to North African scorpion venom evaluated by skin test and specific IgE. J Allergy Clin Immunol. Jun. 1997;99(6 Pt 1):851-3. 4 pages.
Li et al., An improved protocol for the preparation of 3-pyridyl- and some arylboronic acids. J Org Chem. Jul. 26, 2002 26;67(15):5394-7.
Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;14(11):S475.Abstract 3029.
Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.
Litt et al., Mucosal delivery of vaccine antigens displayed on the surface of *Lactococcus lactis*. Immunology Lett. 1999:69(1):61. Abstract #11.26.
Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.
Loesche et al., Treatment paradigms in periodontal disease. Compend Contin Educ Dent. Mar. 1997;18(3):221-6, 228-30, 232 passim; quiz 234. Review.
Luger et al., Evidence for an epidermal cytokine network. J Invest Dermatol. Dec. 1990;95(6 Suppl):100S-104S.
Luskin et al., Olefinic Derivatives of 2,4-Diamino-s-triazines. J Org Chem. 1958;23:1032-37.
Macchia et al., Synthesis and antiviral properties of 9-[(2-methyleneaminoxyethoxy)methyl]guanine derivatives as novel Acyclovir analogues. Farmaco. Feb. 2000; 55(2):104-8.
Majeski et al., Action of venom from the brown recluse spider (*Loxosceles reclusa*) on human neutrophils. Toxicon. 1977;15(5):423-7.
Makarenkova et al., Identification of delta- and mu-type opioid receptors on human and murine dendritic cells. J Neuroimmunol. 2001;117:68-77.
Male et al., Introduction to the Immune System. In: Immunology. Elsevier. 2006:6-7.
Masihi, Progress on novel immunomodulatory agents for HIV-1 infection and other infectious diseases. Expert Opin Ther Patents. 2003;13(6):867-82.
Masiukiewicz et al., Scalable Syntheses of $N^{\alpha}$-Benzyloxycarbonyl-$_L$-Ornithine and of $N^{\alpha}$-(9-Fluorenylmethoxy)Carbonyl-$_L$-Ornithine. Org Prep Proced Int. 2002;34:531-37.
Mataka et al., Condensation reaction of 3,4-Dibenzoy1-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.
Mathur et al., Cell-mediated immune system regulation in periodontal diseases. Crit Rev Oral Biol Med. 1997;8(1):76-89.
Maynor et al., Brown recluse spider envenomation: a prospective trial of hyperbaric oxygen therapy. Acad Emerg Med. Mar. 1997;4(3):184-92.
Mbow et al., Small molecule and biologic modulators of the immune response to hepatitis C virus. Mini Rev Med Chem. May 2006;6(5):527-31.
McCarthy et al., Opioids, opioid receptors, and the immune response. Drug & Alcohol Dependence. 2001;62:111-23.
McKennon et al., A Convenient Reduction of Amino Acids and Their Derivatives. J Org Chem. 1993;58:3568-71.
McLaughlin et al., Opioid growth factor (OGF) inhibits the progression of human squamous cell carcinoma of the head and neck transplanted into nude mice. Cancer Lett. 2003;199:209-17.
Medzhitov, Toll-Like Receptors and Innate Immunity. Nature Rev Immunol. 2001;1:135-45.
Mee et al., Stille coupling made easier—the synergic effect of copper(I) salts and the fluoride ion. Angew Chem. 2004;116:1152-56.
Merigian et al., Envenomation From the Brown Recluse Spider: Review of Mechanism and Treatment Options. Am J Ther. Oct. 1996;3(10):724-734.
Miller et al., Imiquimod applied topically: a novel immune response modifier and new class of drug. Int J Immunopharmacol. Jan. 1999;21(1):1-14.
Minakawa et al., Nucleosides and Nucleotides. 184. Synthesis and Conformational Investigation of Anti-Fixed 3-Deaza-3-halopurine Ribonucleosides. J Org Chem. 1999;64:7158-72.
Moebius et al., The mysteries of sigma receptors: new family members reveal a role in cholesterol synthesis. Trends Pharmacol Sci. Mar. 1997;18(3):67-70.
Moldoveanu et al., Poly-L-lysine as a potential mucosal adjuvant. Immunology Lett. 1999;69(1):62. Abstract #11.28.
Mollick et al., MUC1-like tandem repeat proteins are broadly immunogenic in cancer patients. Cancer Immun. Mar. 17, 2003;3:3. 17 pages.
Moody et al., Lipoxygenase inhibitors prevent lung carcinogenesis and inhibit non-small cell lung cancer growth. Exp Lung Res. Jul.-Aug. 1998;24(4):617-28.
Moraczewski et al., Using Hydrogen Bonding to Control Carbamate C-N Rotamer Equilibria. Org Chem. Oct. 16, 1998;63(21):7258-7262.
Mosbech et al., [Allergy to insect stings] Ugeskr Laeger. Oct. 28, 1991;153(44):3067-71. Danish.
Muller et al., An improved one-pot procedure for the synthesis of alkynes from aldehydes. Synlett. 1996;6:521-522.
Mutschler et al., 9.2 Anti-infectives. In: Drug Actions: Basic Principles and Therapeutic Aspects. 1995:515-80.
Muzio et al., Differential expression and regulation of toll-like receptors (TLR) in human leukocytes: selective expression of TLR3 in dendritic cells. J Immunol. Jun. 1, 2000;164(11):5998-6004.
Nagarajan et al., Condensed heterotricycles: synthesis of pyrazolo[3,4-c]quinoline derivatives. Indian Journal of Chemistry. 1992;31B:316-321.
Nagase et al., Expression and function of Toll-like receptors in eosinophils: activation by Toll-like receptor 7 ligand. J Immunol. Oct. 15, 2003;171(8):3977-82.
Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.
Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-70.
Osol et al., Chapter 27: Structure-Activtiy Relationship and Drug Design. In: Remington's Pharmaceutical Sciences. 16th Ed. Mach Publishing. 1980:420-35.
Ottonello et al., Sulphonamides as anti-inflammatory agents: old drugs for new therapeutic strategies in neutrophilic inflammation? Clin Sci (Lond). Mar. 1995;88(3):331-6.
Ozinsky et al., The repertoire for pattern recognition of pathogens by the innate immune system is defined by cooperation between Toll-like receptors. Proc. Nat. Acad. Sci. 2000; 97(25):13766-71.
Page et al., Advances in the pathogenesis of periodontitis: summary of developments, clinical implications and future directions. Periodontal 2000. Jun. 1997;14:216-48.
Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.
Park et al., Sodium Dithionite Reduction of Nitroarenes Using Viologen as an Electron Phase-Transfer Catalyst. Tetrahedron Lett. 1993;34(46):7445-46.
Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.
Patrick et al., Paragraph 10.3: Drug optimization: strategies in drug design. In: An Introduction to Medicinal Chemistry. Oxford: Oxford University Press. Jan. 2005. 200-218.
Pavletic et al., Outcome of allogeneic stem cell transplantation for B cell chronic lymphocytic leukemia. Bone Marrow Transplant. Apr. 2000;25(7):717-22.
Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.
Payvandi et al., Exogenous and Endogenous IL-10 Regulate IFN-$\alpha$ Production by Peripheral Blood Mononuclear Cells in Response to Viral Stimulation. J Immunol. 1998;160:5861-68.
Peschke et al., Synthesis and in vitro characterization of new growth hormone secretagogues derived from ipamorelin with dipeptidomimetic N-terminals. Eur J Med Chem. 1999;34:363-380.
Peterson et al., The opioid-cytokine connection. J Neuroimmunol. 1998;83:63-69.
Phillips et al., Therapy of brown spider envenomation: a controlled trial of hyperbaric oxygen, dapsone, and cyproheptadine. Ann Emerg Med. Mar. 1995;25(3):363-8.
Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.
Poljakovic et al., iNOS and COX-2 immunoreactivity in the mice bladder and kidney after bacterial instillation. Immunology Lett. 1999;69(1):122. Abstract #31.5.
Powell et al., Compendium of excipients for parenteral formulations. PDA J Pharm Sci Technol. Sep.-Oct. 1998;52(5):238-311.
Prelog et al., Cycloalkeno-pyridine. Hely Chem Acta. 1945;28:1684-93. German.
Rees et al., Brown recluse spider bites. A comparison of early surgical excision versus dapsone and delayed surgical excision. Ann Surg. Nov. 1985;202(5):659-63.
Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.
Rhodes, Discovery of immunopotentiatory drugs: current and future strategies. Clin Exp Immunol. Dec. 2002;130(3):363-9.
Ribera et al., "Spontaneous" complete remissions in chronic lymphocytic leukemia: report of three cases and review of the literature. Blood Cells. 1987;12(2):471-79.
Ritter et al., A new reaction of nitriles; amides from alkenes and mononitriles. J Am Chem Soc. Dec. 1948;70(12):4045-8.
Rocca et al., Carbolines. Part VII. Ansidines, Convenient tools to synthesize fficien-$\beta$-carbolines. J Heterocyclic Chem. 1995;32:1171-1175.
Rocca et al., Connection between metalation and cross-coupling strategies. Anew convergent route to azacarbazoles. Tetrahedron. 1993;49(1):49-64.
Rollins, Chemokines. Blood. Aug. 1, 1997;90(3):909-28. Review.
Rosenberg et al., Treatment of 283 consecutive patients with metastatic melanoma or renal cell cancer using high-dose bolus interleukin 2. JAMA. Mar. 23-30, 1994;271(12):907-13.
Rothel et al., The use of recombinant ovine IL-1beta and TNF-alpha as natural adjuvants and their physiological effects in vivo. Immunol Cell Biol. Apr. 1998;76(2):167-72.
Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.
Royals et al., Studies in mixed ester condensations. IV. Acylations with methyl dimethoxyacetate. J Am Chem Soc. 1956;78:4161-4164.
Rozman et al., Chronic lymphocytic leukemia. N Engl J Med. Oct. 19, 1995;333(16):1052-7.
Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.
Salaun et al., TLR3 Can Directly Trigger Apoptosis in Human Cancer Cells. J of Immunology. 2006;176:4894-901.
Salemink, Uber 2-Propyl-1- Und 2-Propyl-Desaza-Adenin. Recueil. 1961;80:545-55. German.
Sambhi et al., Local production of tumor necrosis factor encoded by recombinant vaccinia virus is effective in controlling viral replication in vivo. Proc Natl Acad Sci U S A. May 1, 1991;88(9):4025-9.
Sams et al., Necrotic arachnidism. J Am Acad Dermatol. Apr. 2001;44(4):561-73; quiz 573-6.
Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.
Scheerlinck, Genetic adjuvants for DNA vaccines. Vaccine. Mar. 21, 2001;19(17-19):2647-56.
Scheuer et al., Application of the Ritter reaction to mesityl oxide and chalcone. J Am Chem Soc. 1957;22:674-676.
Schofield et al., Reply. Low-Dose Interferon-alpha in Chronic Myeloid Leukemia. Ann Internal Med. 1995;122(9):728-29. 1 page.
Schwandner of al., Peptidoglycan- and lipoteichoic acid-induced cell activation is mediated by toll-like receptor 2. J Biol Chem. Jun. 18, 1999;274(25):17406-9.
Seeman et al., Steric and Conformational Effects in Nicotine Chemistry. J Org Chem. 1981;46:3040-48.
Serrat et al., A highly efficient and straightforward stereoselective synthesis of novel chiral $\alpha$-acetylenic ketones. Tetrahedron: Assymmetry. 1999;10:3417-30.
Severa et al., Sensitization to TLR7 agonist in IFN-beta-preactivated dendritic cells. J Immunol. May 15, 2007;178(10):6208-16.
Seymour et al., Cellular immunity and hypersensitivity as components of periodontal destruction. Oral Dis. Mar. 1996;2(1):96-101. Review.
Shelburne et al., Quantitation of Bacteroids forsythus in subgingival plaque comparison on immunoassay and quantitative polymerase chain reaction. J Microbiol Methods. 2000;39:97-107.
Sidky et al., Inhibition of murine tumor growth by an interferon-inducing imidazoquinolinamine. Cancer Res. Jul. 1, 1992;52(13):3528-33.
Siegal et al., The nature of the principal type 1 interferon-producing cells in human blood. Science. Jun. 11, 1999;284(5421):1835-7.
Sletzinger et al., The Synthesis of Isomethadone. J Am Chem Soc. 1952;74:5619-20.
Smith et al., The role of polymorphonuclear leukocytes in the lesion caused by the venom of the brown spider, *Loxosceles reclusa*. Lab Invest. Jan. 1970;22(1):90-3.
Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80/1933. 1980:76-8.
Sommer et al., Recent Findings on How Proinflammatory Cytokines Cause Pain: Peripheral Mechanisms in Inflammatory and Neuropathic Hyperalgesia. Neurosci Letts. 2004;361:184-87.
Sonogashira et al., A convenient synthesis of acetylenes: catalytic substitutions of acetylenic hydrogen with bromoalkenes, lodoarenes, and bromopyridines. Tetrahedron Letts. 1975;50:4467-4470.
Soria et al., Effect of food on the pharmacokinetics and bioavailability of oral imiquimod relative to a subcutaneous dose. Int J Clin Pharmacol Ther. Oct. 2000;38(10):476-81.
Spivey et al., Configurationally stable biaryl analogues of 4-(dimethylamino)pyridine: A novel class of chiral nucleophilic catalysts. J Org Chem. 1999;64:9430-9443.
Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.
Stack, Images in clinical medicine. *Latrodectus mactans*. N Engl J Med. Jun. 5, 1997;336(23):1649.
Stanley, Imiquimod and the imidazoquinolones: mechanism of action and therapeutic potential. Clin Exp Dermatol. Oct. 2002;27(7):571-7. Review.
Stashenko et al., Periapical inflammatory responses and their modulation. Crit Rev Oral Biol Med. 1998;9(4):498-521.
Steele et al., Lipoxygenase inhibitors as potential cancer chemopreventives. Cancer Epidemiol Biomarkers Prey. May 1999;8(5):467-83.
Steele et al., Potential use of lipoxygenase inhibitors for cancer chemoprevention. Expert Opin Investig Drugs. Sep. 2000;9(9):2121-38.
Steinmann et al., Topical imiquimod treatment of a cutaneous melanoma metastasis. J Am Acad Dermatol. Sep. 2000;43(3):555-6.
Stewart et al., Synthesis of a Carba-analog of *S*-Acetyl Coenzyme A,Acetonyl-dethio Coenzyme A; an Effective Inhibitor of Citrate Synthase. Liebigs Ann Chem. 1978:57-65.
Stillings et al., Substituted 1,3,4-thiadiazoles with anticonvulsant activity. 2. Aminoalkyl derivatives. J Med Chem. Nov. 1986;29(11):2280-4.
Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.
Stringfellow, Induction of interferon with low molecular weight compounds: fluorenone esters, ethers (tilorone), and pyrimidinones. Methods Enzymol. 1981;78(Pt A):262-84.
Ströher et al., Progress towards the treatment of Ebola haemorrhagic fever. Expert Opin Investig Drugs. Dec. 2006;15(12):1523-35.
Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;14(11):S475. Abstract 3030.
Surrey et al., The Synthesis of Some 3-Nitro- and 3-Amino-4-dialkylaminoalkylaminoquinoline Derivatives. J Am Chem Soc. 1951;73:2413-16.
Takeichi et al., Cytokine profiles of T-lymphocytes from gingival tissues with pathological pocketing. J Dent Res. Aug. 2000;79(8):1548-55.
Takeshita et al., Signal transduction pathways mediated by the interaction of CpG DNA with Toll-like receptor 9. Semin Immunol. Feb. 2004;16(1):17-22.
Takeuchi et al., Discrimination of bacterial lipoproteins by Toll-like receptor 6. Int. Immunol. Jul. 2001;13(7):933-40.
Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-61.
Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.
Testerman et al., Cytokine induction by the immunomodulators imiquimod and S-27609. J Leukoc Biol. Sep. 1995;58(3):365-72.
Thesing et al., [Darstellung and Eigenschaften des $\Delta^1$-Pyrrolin-*N*-oxyds.]. Chem Ber. 1959;92:1748-55. German.
Thiruvikraman et al., Synthesis and reactions of pyrazolo-[3,4-c]quinoline derivatives. Indian Journal of Chemistry. 1987;26B:695-696.
Tomai et al., Imiquimod: in vivo and in vitro characteristics and toxicology. In: Cutaneous Infection and Therapy. Aly et al., eds. Marcel Dekkar, Inc., New York. 1997:405-15.
Tomioka et al., Asymmetric Alkylation of α-Alkyl β-Keto Esters. J Am Chem Soc. 1984;106:2718-19.
Totterman et al., Phorbol ester-induced differentiation of chronic lymphocytic leukaemia cells. Nature. Nov. 13, 1980;288(5787):176-8.
Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.
Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.
Urosevic et al., Imiquimod treatment induces expression of opioid growth factor receptor: a novel tumor antigen induced by interferon-alpha? Clin Cancer Res. Aug. 1, 2004;10(15):4959-70.
Van De Kerhof, New Immunomodulatory Drugs. In: Skin and Environment: Perception and Protection. Ring et al., eds., 10th EADV Congress, Oct. 10-14, Munich, Germany. 2001:1:343-48.
Vasilakos et al., Adjuvant Activities of Immune Response Modifier R-848: Comparison with CoG ODN. Cell Immunol. 2000;204:64-74.
Vieweg et al., Tumor vaccines: from gene therapy to dendritic cells-the emerging frontier. Urol Clin North Am. Aug. 2003;30(3):633-43.
Vilcek, The cytokines: An overview. In: The Cytokine Handbook, Fourth Ed. M. Lotze and A.W. Thompson (eds.), 2003;1:3-14.
Volhardt, 18-5. Amides: The Least-Reactive Carboxylic Acid Derivatives. Organic Chemistry. 1987:813.
Vollmer et al., Highly immunostimulatory CpG-free oligodeoxynucleotides for activation of human leukocytes. Antisense Nucleic Acid Drug Dev. Jun. 2002;12(3):165-75.
Wagner et al., Induction of cytokines in cynomolgus monkeys by the immune response modifiers, imiquimod, S-27609 and S-28463. Cytokine. Nov. 1997;9(11):837-45.
Wagner et al., Modulation of TH1 and TH2 Cytokine Production with the Immune Response Modifiers, R-848 and Imiguimod. Cellular Immunology. 1999;191:10-19.
Wang, Structure and Chemistry of 4-Hydroxy-6-methyl-2-pyridone. J Heterocyclic Chem. 1970;7:389-92.
Warren et al., Macrophage Growth Factor CSF-1 Stimulates Human Monocyte Production of Interferon, Tumor Necrosis Factor, and Colony Stimulating Activity. J Immunol. 1986;137(7):2281-85.
Wasserman et al., Loxoscelism and necrotic arachnidism. J Toxicol Clin Toxicol. 1983-1984;21(4-5):451-72.
Wedlock et al., Physiological effects and adjuvanticity of recombinant brushtail possum TNF-alpha. Immunol Cell Biol. Feb. 1999;77(1):28-33.
Wells, Additivity of Mutational Effects in Proteins. Biochemistry. 1990;29(37):8509-17.
Wermuth, Molecular Variations Based on Isosteric Replacements. Practice of Medicinal Chemistry.1996:203-37.
Wexler et al., Accurate identification of experimental pulmonary metastases. J Natl Cancer Inst. Apr. 1966;36(4):641-5.
Wibaut et al., Syntheses of 3,4-Dimethylpyridine, 2,3-Dimethylpridine and 2-Methyl-3-Ethylpyridine. Rec Tray Chim. 1944;63:231-38.
Wierda et al., CD40-ligand (CD154) gene therapy for chronic lymphocytic leukemia. Blood. Nov. 1, 2000;96(9):2917-24.
Wieseler-Frank et al., Central proinflammatory cytokines and pain enhancement. Neurosignals. 2005;14(4):166-74.
Williams et al., Grignard Reactions to Chiral Oxazolidine Aldehydes. Tetrahedron. 1996;52:11673-94.
Wilson et al., Spiders and spider bites. Dermatol Clin. Apr. 1990;8(2):277-86.

Wozniak et al., The amination of 3-nitro-1, 5-naphthyridines by liquid ammonia/potassium permanganate1,2. A new and convenient animation method. J. Royal Netherlands Chem Soc. Dec. 12, 1983(102):511-3.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and *Drosophila nicotinic* receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

* cited by examiner

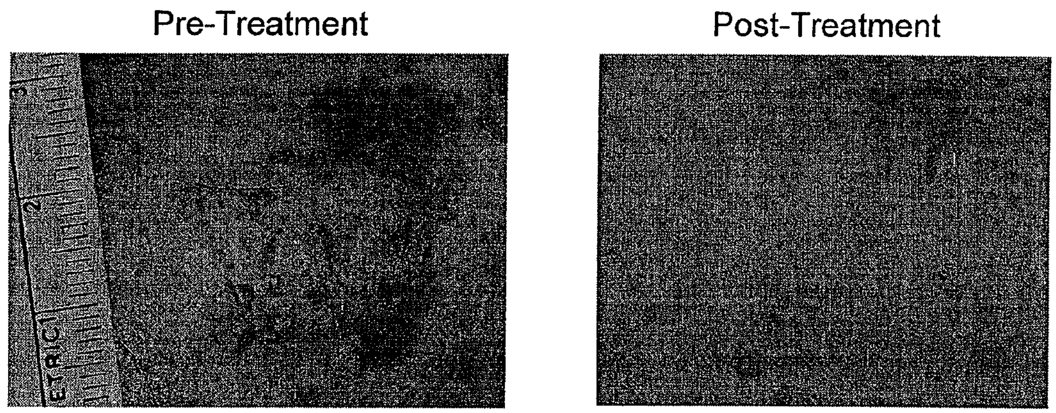
FIG. 6A
FIG. 6B
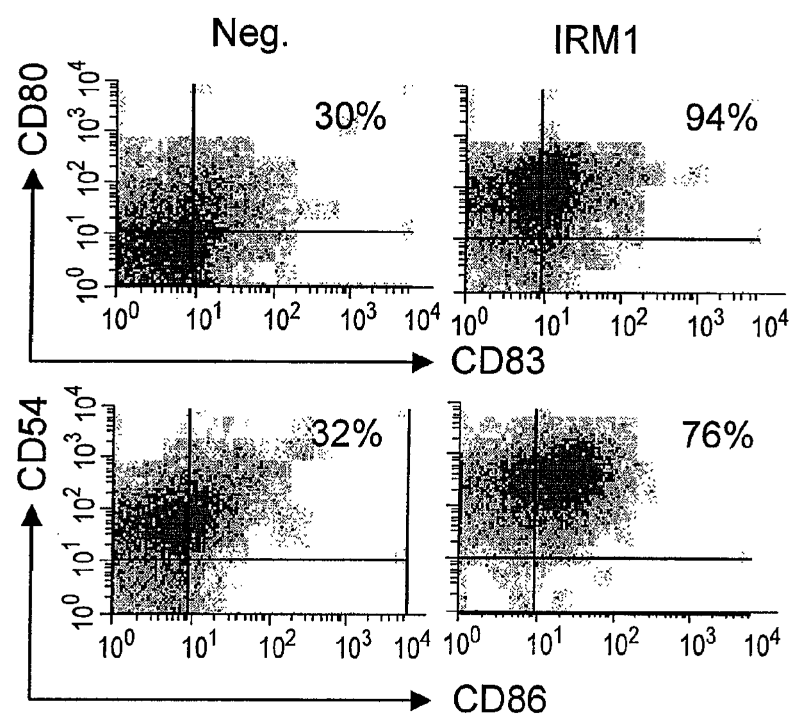
FIG. 7

TREATMENT FOR CD5$^+$ B CELL LYMPHOMA

CROSS-REFERENCE TO RELATED APPLICATION

This application is a continuation of U.S. patent application Ser. No. 10/933,594, filed Sep. 3, 2004 which claims the benefit to U.S. Provisional Patent Application Ser. No. 60/500,478, filed Sep. 5, 2003, and U.S. Provisional Application Ser. No. 60/561,440, filed Apr. 12, 2004.

BACKGROUND

The peripheral B cell neoplasm chronic lymphoid leukemia/small lymphocytic lymphoma represents the most common lymphoid leukemia. As the name implies, presentation can be as either leukemia or lymphoma. However, the two presentations of this neoplasm, chronic lymphocytic leukemia (CLL) and small lymphocytic lymphoma (SLL), are morphologically, phenotypically, and genotypically indistinguishable, differing only in the degree of peripheral blood lymphocytosis.

CLL is the most common leukemia of adults in the Western world. In CLL, the peripheral blood contains small, round lymphocytes with scant cytoplasm. Involvement of the bone marrow is observed in all cases of CLL and most cases of SLL, taking the form of interstitial infiltrates or nonparatubular aggregates of small lymphocytes. The tumor cells in CLL and SLL express the pan B cell markers CD29 and CD20. In addition, CD5—a T cell marker that is expressed only on a small subset of normal B cells—is present on the tumor cells. The immunophenotype of CLL cells is unique. CLL cells co-express the B lymphocyte lineage marker CD19 and the T lymphocyte marker CD5. CLL cells also exhibit a characteristic level of expression of immunoglobulin receptor. Tumor cells typically also have low-level surface expression of Ig heavy chain, with either kappa or lambda light chains.

CLL is a clonal malignancy of B lymphocytes. The disease is usually indolent, with slowly progressive accumulation of long-lived small lymphocytes that are immunoincompetent and respond poorly to antigenic stimulation. CLL is incurable with conventional cytotoxic chemotherapy (Cheson et al., *Blood* 1996; 87:4990-4997; and Keating et al., *Blood* 1993; 81:2878-2884). The hallmark of CLL is isolated lymphocytosis. The white blood cell count is usually greater than 20,000/μL and may be markedly elevated to several hundred thousand. The diagnostic requirement for CLL is an absolute lymphocyte count of greater than 4000/mm$^3$. CLL is manifested clinically by immunosuppression, bone marrow failure, and organ infiltration with lymphocytes. Immunodeficiency is also related to inadequate antibody production by the abnormal B cells. With advanced disease, CLL may cause damage by direct tissue infiltration.

In some cases, patients may develop cutaneous lymphoma deposits—erythomatous lesions on the skin. The lesions may contain an atypical lymphoid dermal infiltrate of small, round B cells.

SUMMARY

It has been found that certain small molecule immune response modifiers (IRMs) can be useful for increasing the expression of molecules on the surface of CD5$^+$ B cell lymphoma cells. Thus, certain IRMs can be used for treating a CD5$^+$ B cell lymphomas such as, for example, chronic lymphocytic leukemia (CLL), small lymphocytic lymphoma (SLL), mantle cell lymphoma, or splenic lymphoma with villous lymphocytes.

Accordingly, the invention provides a method of treating a CD5$^+$ B cell lymphoma. Generally, the method includes administering to a subject an IRM compound in an amount effective to ameliorate at least one symptom or clinical sign of the CD5$^+$ B cell lymphoma. In some embodiments, administering the IRM compound may result in at least a 50% decrease in peripheral blood lymphocytes, lymphadenopathy, or splenomegaly for at least two months. In other embodiments, administering the IRM compound can inhibit or even prevent the development of progressive disease, wherein progressive disease is at least a 50% increase in circulating lymphocytes or a progression to a more aggressive histology. In still other embodiments, administering the IRM compound can resolve nodular, erythematous lesions associated with CD5$^+$ B cell lymphoma.

In another aspect, the invention provides a method of increasing the expression of at least one cell surface molecule of CD5$^+$ B cell lymphoma cells. Generally, the method includes contacting the CD5$^+$ B cell lymphoma cells with at least one IRM effective for increasing the expression of at least one cell surface molecule of the CD5$^+$ B cell lymphoma cells. In some embodiments, the cell surface molecule may be a costimulatory molecule.

In another aspect, the present invention also provides a method of stimulating CD5$^+$ B cell lymphoma cells to produce a cytokine by contacting the CD5$^+$ B cell lymphoma cells with an IRM effective for inducing production of a cytokine above a level produced by the CD5$^+$ B cell lymphoma cells not contacted by the IRM. In some embodiments, the cytokine may be IL-1β, IL-6, IL-8, IL-10, IL-12, TNF-α, GM-CSF, or combinations thereof.

In another aspect, the invention provides a method of increasing proliferation of CD5$^+$ B cell lymphoma-specific cytotoxic T cells. Generally, the method includes contacting CD5$^+$ B cell lymphoma cells with an IRM effective to increase the expression of at least one costimulatory molecule on the surface of CD5$^+$ B cell lymphoma cells, and then contacting CD8+ T cells with the CD5$^+$ B cell lymphoma cells, thereby activating the CD8$^+$ T cells; wherein the activated T cells are CD5$^+$ B cell lymphoma-specific cytotoxic T cells and demonstrate increased proliferation compared to T cells contacted with CD5$^+$ B cell lymphoma cells that have not been contacted with an IRM.

In some embodiments, the CD8$^+$ T cells are CD5$^+$ B cell lymphoma cell-specific. In other embodiments, the CD8$^+$ T cells are naive.

In some embodiments, the IRM compound may be administered to a subject diagnosed as having a CD5$^+$ B cell lymphoma so that the activated CD5$^+$ B cell lymphoma-specific cytotoxic T cells are autologous CD5$^+$ B cell lymphoma-specific cytotoxic T cells.

In some embodiments, the CD5$^+$ B cell lymphoma cells may be further contacted with one or more additional immunomodulating agents such as, for example, IL-2 and/or a protein kinase C agonist.

In another aspect, the present invention also provides a method of increasing the killing of CD5$^+$ B cell lymphoma cells by cytotoxic T cells. Generally, the method includes contacting CD5$^+$ B cell lymphoma cells with an IRM effective to increase the expression of at least one costimulatory molecule on the cell surface of the CD5$^+$ lymphoma cells, and then contacting CD8$^+$ T cells with the CD5$^+$ B cell lymphoma cells, thereby activating the CD8$^+$ T cells; wherein the activated CD8$^+$ T cells are CD5$^+$ B cell lymphoma-specific cytotoxic T cells and demonstrate increased killing of $CD5^+$ B cell lymphoma cells compared to T cells contacted with $CD5^+$ B cell lymphoma cells that have not been contacted with an IRM.

In some embodiments, the $CD8^+$ T cells are $CD5^+$ B cell lymphoma cell-specific. In other embodiments, the $CD8^+$ T cells are naive.

In some embodiments, the IRM compound may be administered to a subject diagnosed as having a $CD5^+$ B cell lymphoma so that the activated $CD5^+$ B cell lymphoma-specific cytotoxic T cells are autologous $CD5^+$ B cell lymphoma-specific cytotoxic T cells.

In some embodiments, the $CD5^+$ B cell lymphoma cells may be further contacted with one or more additional immunomodulating agents such as, for example, IL-2 and/or a protein kinase C agonist.

In another aspect, the present invention also provides a method of treating a subject suffering from a $CD5^+$ B cell lymphoma including administering to the subject an IRM effective to increase the expression of at least one cell surface molecule of the $CD5^+$ B cell lymphoma cells.

In another aspect, the present invention also provides a vaccine that includes isolated $CD5^+$ B cell lymphoma cells, or an immunologically active portion thereof, wherein the isolated $CD5^+$ B cell lymphoma cells have been contacted with an IRM effective to increase the expression of at least one cell surface molecule of the $CD5^+$ B cell lymphoma cells. In certain embodiments, the $CD5^+$ B cell lymphoma cells may be further contacted with one or more additional immunomodulatory agents such as, for example, IL-2 and/or a protein kinase C agonist.

In another aspect, the present invention also provides a method of preparing a vaccine including contacting isolated $CD5^+$ B cell lymphoma cells with an IRM effective to increase the expression of at least one molecule on the surface of the $CD5^+$ B cell lymphoma cells. Some embodiments may include further contacting isolated $CD5^+$ B cell lymphoma cells with one or more additional immunomodulatory agents such as, for example, IL-2 or a protein kinase C agonist. In other embodiments, the isolated $CD5^+$ B cell lymphoma cells may be derived from a subject diagnosed as having CLL or SLL.

In some embodiments, the $CD5^+$ B cell lymphoma cells may be chronic lymphocytic leukemia (CLL) cells, small lymphocytic lymphoma cells (SLL), mantle cell lymphoma cells, splenic lymphoma with villous lymphocytes, or combinations thereof.

In some embodiments, the IRM is a TLR7 agonist. In some embodiments, the IRM is a TLR8 agonist. In still other embodiments, the IRM compound may be an agonist of both TLR7 and TLR8.

In some embodiments, the IRM may be an imidazoquinoline amine, a tetrahydroimidazoquinoline amine, an imidazopyridine amine, a 1,2-bridged imidazoquinoline amine, a 6,7-fused cycloalkylimidazopyridine amine, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, or a thiazolonaphthyridine amine. In certain embodiments, the IRM is an imidazoquinoline amine such as, for example, 1-(2-methylpropyl)-1H-imidazo[4,5-c]quinolin-4-amine. In alternative embodiments, the IRM is a tetrahydroimidazoquinoline amine such as, for example, 4-amino-2-(ethoxymethyl)-α,α-dimethyl-6,7,8,9-tetrahydro-1H-imidazo[4,5-c]quinoline-1-ethanol hydrate. In still other embodiments, the IRM is a sulfonamide substituted imidazoquinoline amine such as, for example, N-[4-(4-amino-2-ethyl-1H-imidazo[4,5-c]quinolin-1-yl)butyl]methanesulfonamide.

In some embodiments, at least one cell surface molecule whose expression is increased may be CD20, CD22, or CD23, and the method further includes administering to the subject a therapeutic agent that has, as a target, the cell surface molecule whose expression is increased. In some embodiments, the expression of more than one cell surface molecule may be increased.

In some embodiments, at least one costimulatory molecule whose expression is increased may be CD40, CD54, CD80, CD83, CD86, CD25, or CD38. In some embodiments, the expression of more than one costimulatory molecule may be increased.

In some embodiments, the $CD5^+$ B cell lymphoma cells may be contacted with an IRM in vitro. In other r embodiments, the $CD5^+$ B cell lymphoma cells may be contacted with an IRM in vivo such as, for example, in an organ, tissue, or blood of a subject.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

BRIEF DESCRIPTION OF THE DRAWINGS

FIGS. 6A-B. Photographs of a lymphomatous skin deposit before treatment (FIG. 6A) and after treatment (FIG. 6B) with an IRM.

FIG. 7. Effect of IRM1 on costimulatory molecule expression by CLL cells.

DETAILED DESCRIPTION OF ILLUSTRATIVE EMBODIMENTS OF THE INVENTION

Figure 1A:
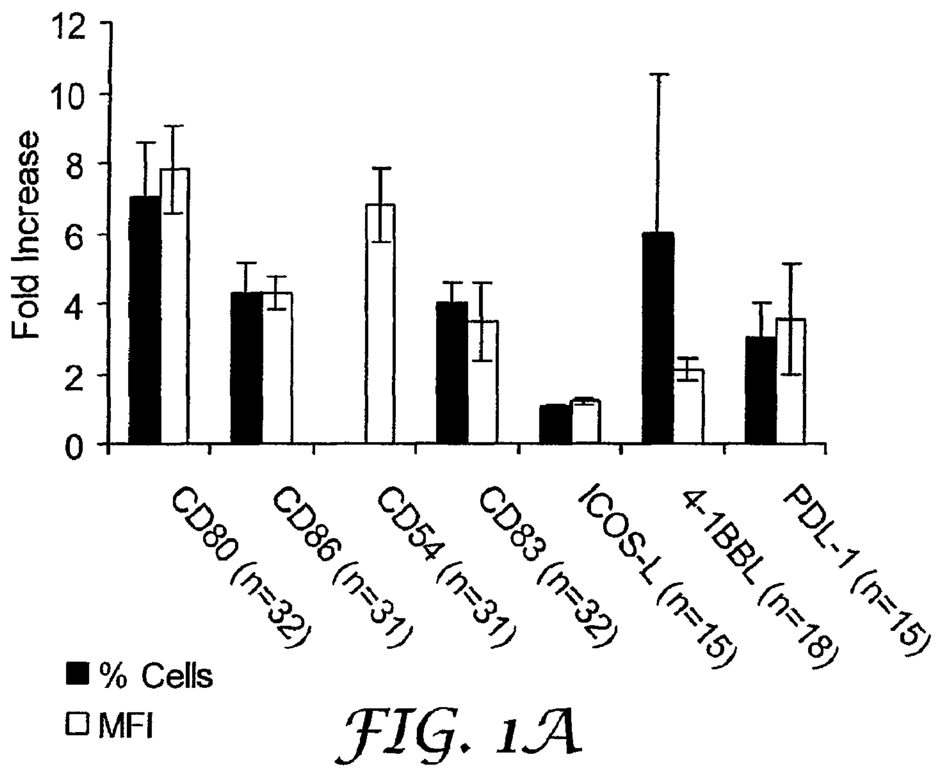
FIGS. 1*a-b*. Enhancement of costimulatory molecule expression on CLL cells by an IRM compound.

The present invention provides methods for treating $CD5^+$ B cell lymphomas such as, for example, chronic lymphocytic leukemia (CLL). While a number of clinical observations suggest that $CD5^+$ B cell lymphoma cells may be subject to T cell mediated immune recognition (see, for example, Ribera et al., *Blood Cells* 1987; 12:471-483; Ziegler-Heitbrock et al., *Blood* 1989; 73:1426-1430; Wierda et al., *Blood* 2000; 96:2917-2924; Gitelson et al., *Clin Cancer Res.* 2003; 99:1656-1665; and Pavletic et al., *Bone Marrow Transplant* 2000; 25:717-722), the weak immunogenicity of $CD5^+$ B cell lymphoma cells has limited development of immunologically based treatment methods and, therefore, contributes to disease progression.

The present invention demonstrates, for the first time, that contacting $CD5^+$ B cell lymphoma cells with an immune response modifier (IRM) compound may be useful for treating $CD5^+$ B cell lymphomas. IRM compounds appear to act through basic immune system mechanisms known as toll-like receptors (TLRs) to induce selected biosynthesis of certain cytokines, chemokines and costimulatory molecules. Thus, certain IRM compounds can selectively induce certain aspects—and/or inhibit other aspects—of the immune system. In particular, IRM compounds may increase the expression of cell surface molecules of $CD5^+$ B cell lymphoma cells, enhance the immunogenicity of $CD5^+$ B cell lymphoma cells, and provide a new immunotherapeutic approach for the treatment of $CD5^+$ B cell lymphomas. In some cases, the cell surface molecule whose expression is increased may be a costimulatory molecule. Increasing the cell surface expression of costimulatory molecules may allow the $CD5^+$ B cell lymphoma cells to become competent antigen presenting cells (APCs) capable of initiating and/or maintaining tumor-reactive T cell activity.

As used herein, the following terms shall have the following meanings:

"Ameliorate" refers to any reduction in the extent, severity, frequency, and/or likelihood of a symptom or clinical sign characteristic of a particular condition.

"$CD5^+$ B cell lymphoma cells" refers to neoplastic cells having a unique immunophenotype that includes co-expression of CD19 and CD5. In addition to expressing the B lymphocyte lineage marker CD19, $CD5^+$ B cell lymphoma cells also express the T lymphocyte marker CD5, which is typically expressed only on a small subset of normal B cells. $CD5^+$ B cell lymphoma cells include, for example, chronic lymphocytic leukemia (CLL) cells, small lymphocytic lymphoma (SLL) cells, mantle cell lymphoma cells, and splenic lymphoma with villous lymphocytes. In some embodiments, the $CD5^+$ B cell lymphoma cells are CLL cells or SLL cells. In certain specific embodiments, the $CD5^+$ B cell lymphoma cells are CLL cells.

"Cell surface molecule" refers to a molecule that is expressed on the surface of a cell and may be used to determine the cell's lineage or otherwise may be used to distinguish one cell or cell type from another.

"Patient" or "Subject" includes, for example, animals such as, but not limited to, humans, non-human primates, rodents, dogs, cats, horses, pigs, sheep, goats, or cows.

"Sign" or "clinical sign" refers to an objective physical finding relating to a particular condition capable of being found by one other than the patient.

"Symptom" refers to any subjective evidence of disease or of a patient's condition.

Unless otherwise specified, "a," "an," "the," and "at least one" are used interchangeably and mean one or more than one.

Certain IRM compounds such as, for example, agonists of TLR7 and/or TLR8 can increase the expression of a number of cell surface molecules (including, e.g., costimulatory molecules) of $CD5^+$ B cell lymphoma cells, which can result in a more potent immune response being raised against the $CD5^+$ B cell lymphoma cells. Thus, increasing expression of cell surface molecules of $CD5^+$ B cell lymphoma cells may be exploited to provide therapies that can slow or stop progression of the disease. In certain embodiments, the therapy may reverse the course of the disease, in some cases even to the point of completely resolving—i.e., curing—the disease.

In addition to having therapeutic utility, $CD5^+$ B cell lymphoma cells having increased expression of one or more costimulatory molecules and/or other cell surface molecules may have diagnostic or investigative utility.

Two signals are required for the induction of cell proliferation and cytokine production in naive T cells. The first signal is the foreign antigen, which is presented by self-major histocompatibility complex (MHC) on the surface of an antigen presenting cell (APC). The antigenic peptide-MHC complex interacts with a T cell receptor (TCR) on the surface of the naive T cell, thereby providing antigen specificity to the immune response. The second signal is a "costimulatory" signal. Costimulatory signals are antigen-independent and are provided to the naive T cell by the APC, through specific receptor-ligand interactions that promote, for example, T cell survival, clonal expansion, cytokine secretion, and effector function.

In the presence of both signals, a productive adaptive immune response may be generated. In the absence of the costimulatory signal, however, lymphocytes may fail to respond effectively to antigen stimulation. Such unresponsiveness of the adaptive immune system can result in immunologic tolerance.

Accordingly, as used herein, "costimulatory molecule" refers to a member of a subset of cell surface molecules whose expression is necessary, in addition to presentation of a MHC I molecule, to generate a productive immune response, but whose expression is not independently sufficient to generate a productive immune response. Examples of costimulatory molecules include, but are not limited to, members of the B7 family (including, for example, B7-1 (CD80), B7-2 (CD86), ICOS-L (B7RP1), and PDL-1), other molecules of the Ig superfamily (including, for example, CD2 and OX2), molecules of the TNF:TNFR subfamily that lack death domains (including, for example, CD40, OX40, CD27, 4-1BB, and CD30), and some integrins (including, for example, VLA-4, ICAM-1, and ICAM-3).

The increased expression of one or more cell surface molecules can be determined using any of many known methods, including any of the methods described herein. For example, such methods include, but are not limited to, flow cytometry, immunohistochemistry, reverse transcriptase polymerase chain reaction (RT-PCR), including quantitative RT-PCR, and Northern blot analysis.

In some embodiments, $CD5^+$ B cell lymphoma cells may be stimulated to increase expression of one or more of CD20, CD22, CD23, CD25, CD38, CD40, CD54, CD80, CD83, or CD86.

In certain embodiments, the $CD5^+$ B cell lymphoma cells may be stimulated to increase expression of a cell surface molecule that is a target of a therapeutic agent such as, for example, a monoclonal antibody that specifically binds to the cell surface molecule. In this way, the increase in cell surface molecule expression may be exploited in a treatment that is targeted against the cell surface molecule. For example, rituximab is a monoclonal antibody that targets CD20 and has been shown to be an effective treatment for non-Hodgkin's lymphoma. Rituximab binds to B cells that express CD20, thereby marking the rituximab-labeled cells for elimination by the immune system. Thus, a treatment that includes, for example, (a) increasing expression of CD20 on $CD5^+$ B cell lymphoma cells, and then (b) administering rituximab may permit rituximab to bind to $CD5^+$ B cell lymphoma cells, thereby marking $CD5^+$ B cell lymphoma cells for elimination by the immune system, and thereby rendering rituximab an effective treatment for $CD5^+$ B cell lymphomas. Additional cell surface molecules whose expression may be increased in CD5$^+$ B cell lymphoma cells, and that may serve as a target for a therapeutic agent include, for example, CD22 and CD23.

In some embodiments, CD5$^+$ B cell lymphoma cells may be stimulated to produce a cytokine by contacting the CD5$^+$ B cell lymphoma cells with an IRM effective to produce the cytokine in an amount that is greater than that produced by CD5$^+$ B cell lymphoma cells not contacted by the IRM. In some embodiments, the IRM compound may be an agonist of one or more TLRs such as, for example, a TLR7 agonist, a TLR8 agonist, or an agonist of both TLR7 and TLR8. The cytokine produced can include, but is not limited to, IL-1β, IL-6, IL-8, IL-10, IL-12, TNF-α, GM-CSF, and combinations thereof.

In some embodiments, the CD5$^+$ B cell lymphoma cells may be contacted with an IRM compound in vitro, for example, in cell culture. In alternative embodiments, CD5$^+$ B cell lymphoma cells may be contacted with an IRM compound in vivo—i.e., the CD5$^+$ B cell lymphoma cells and IRM compound may be contacted in an organ, a tissue, or the blood. In such cases, the CD5$^+$ B cell lymphoma cells may be contacted with an IRM compound in a subject by, for example, administering an IRM compound to a subject diagnosed as having a CD5$^+$ B cell lymphoma. Administration of the IRM directly to the subject allows the CD5$^+$ B cell lymphoma cells, after being contacted with IRM, to activate autologous T cells—i.e., the subject's own T cells—thereby generating a T cell-dependent immune response against the CD5$^+$ B cell lymphoma cells. By exploiting the subject's own T cell population to generate an immunological response to the CD5$^+$ B cell lymphoma cells, one may be able to reduce or even eliminate certain risks associated with therapies that involve administering heterologous biological material (e.g., inflammation, rejection, etc.).

The IRM compounds may be administered via any suitable means, including, for example, parenterally, transdermally, intranasally, and orally. Suitable formulations for delivery of IRM compounds are described in detail below.

In some embodiments, an IRM effective to increase the expression of at least one costimulatory molecule on the cell surface of CD5$^+$ B cell lymphoma cells can be administered to a subject suffering from a CD5$^+$ B cell lymphoma in a clinically effective amount. As used herein a "clinically effective amount" is an amount effective to demonstrate one or more indications of clinical improvement. Such indications of clinical improvement can include any of those measurements applied in medical practice or laboratory research. See, for example, Cheson et al., National Cancer Institute-sponsored Working Group guidelines for chronic lymphocytic leukemia: revised guidelines for diagnosis and treatment. *Blood.* 1996; 87:4990-4997. For example, a clinically effective amount may be an amount effective to obtain a partial response (PR). As used herein, a "partial response" is at least about a 50% decrease in peripheral blood lymphocytes, lymphadenopathy, and/or splenomegaly, for at least two months. A clinically effective amount may be an amount effective to obtain a complete response (CR). As used herein, a "complete response" is the absence of detectable leukemia or lymphoma cells. A clinically effective amount may be an amount effective to prevent progressive disease (PD). As used herein, "progressive disease" is at least about a 50% increase in circulating lymphocytes or the progression to a more aggressive histology, as determined by known pathological criteria. A clinically effective amount may be an amount effective to increase the likelihood or extent of long-term survival. Alternatively, a clinically effective amount may be an amount that reduces or ameliorates at least one symptom or clinical sign associated with a CD5$^+$ B cell lymphoma. For example, a clinically effective amount may be an amount sufficient to reduce the severity, extent, or number of cutaneous lymphoma deposits.

In some embodiments, the effect of contacting one or more IRMs with CD5$^+$ B cell lymphoma cells may be enhanced by further contacting the CD5$^+$ B cell lymphoma cells with one or more additional immunomodulatory agents. In such embodiments, the IRM and one or more additional immunomodulatory agents may be considered a combination such as, for example, a therapeutic combination. Components of such a combination may be said to be delivered "in combination" with one another if the components are provided in any manner that permits the biological effect of contacting one component with CD5$^+$ B cell lymphoma cells to be sustained at least until another component is contacted with the CD5$^+$ B cell lymphoma cells. Thus, components may be delivered in combination with one another even if they are provided in separate formulations, delivered via different routes of administration, and/or administered at different times.

A suitable immunomodulatory agent may include, for example, interleukin-2 ("IL-2"). IL-2 is a growth factor for antigen-stimulated T lymphocytes and is responsible for T cell clonal expansion after antigen recognition. IL-2 can be obtained from any of many well-known sources. For example, clinical grade IL-2 can be commercially purchased, for example, from Chiron Corporation, San Francisco, Calif.

In some embodiments, the CD5$^+$ B cell lymphoma cells may be contacted with IL-2 in vitro, for example, in cell culture. In alternative embodiments, CD5$^+$ B cell lymphoma cells may be contacted with IL-2 in vivo—i.e., the CD5$^+$ B cell lymphoma cells and IL-2 may be contacted in an organ, a tissue, or the blood. In such cases, the CD5$^+$ B cell lymphoma cells may be contacted with IL-2 in a subject by, for example, administering IL-2 to a subject suffering from a CD5$^+$ B cell lymphoma. The IL-2 may be administered via any suitable means, including, for example, parenterally, transdermally, intranasally, and orally. Suitable formulations for delivery of IL-2 are described below.

The precise amount of IL-2 used in any one embodiment will vary according to factors known in the art, including but not limited to, the physical and chemical nature of the IL-2, the physical and chemical nature of the IRM or IRMs provided in combination with the IL-2, the intended dosing regimen, the state of the subject's immune system (e.g., suppressed, compromised, stimulated), the method of administering the IL-2, whether any additional immunomodulatory agents are being administered in combination with the IL-2, and the species to which the formulation is being administered. Accordingly it is not practical to set forth generally the amount that constitutes an amount of IL-2 effective for all possible applications. Those of ordinary skill in the art, however, can readily determine the appropriate amount with due consideration of such factors. For example, IL-2 may be administered to a subject following procedures similar to those outlined by Rosenberg et al. on the administration of IL-2 for the treatment of melanoma and renal cell carcinoma. Rosenberg et al., *JAMA,* 1994; 271:907-913.

Another suitable immunomodulatory agent may include, for example, a protein kinase C (PKC) agonist. Examples of PKC agonists include, but are not limited to, phorbol esters (Totterman et al., *Nature,* 1980; 288:176-178) and bryostatin-1 (Drexler et al., *Blood,* 1989; 74: 1747-1757). Physiological ligands of molecules on the surface of lymphoma cells also can serve as PKC agonists by inducing signal transduction through the cell surface molecules, resulting in the activation of members of the PKC family of proteins. For example, antibodies against certain molecules on the surface of lymphoma cells can also serve as PKC agonists. Such antibodies include, for example, antibodies against MHC class I molecules and antibodies to surface Ig.

In some embodiments, the $CD5^+$ B cell lymphoma cells may be contacted with a PKC agonist in vitro, for example, in cell culture. In alternative embodiments, $CD5^+$ B cell lymphoma cells may be contacted with a PKC agonist in vivo—i.e., the $CD5^+$ B cell lymphoma cells and a PKC agonist may be contacted in an organ, a tissue, or the blood. In such cases, the $CD5^+$ B cell lymphoma cells may be contacted with a PKC agonist in a subject by, for example, administering a PKC agonist to a subject suffering from a $CD5^+$ B cell lymphoma. The PKC agonist may be administered via any suitable means, including, for example, parenterally, transdermally, intranasally, and orally. Suitable formulations for delivery of a PKC agonist are described below.

The precise amount of a PKC agonist used in any one embodiment will vary according to factors known in the art including but not limited to the physical and chemical nature of the PKC agonist, the physical and chemical nature of the IRM or IRMs provided in combination with the PKC agonist, the intended dosing regimen, the state of the subject's immune system (e.g., suppressed, compromised, stimulated), the method of administering the PKC agonist, whether any additional immunomodulatory agents are being administered in combination with the PKC agonist, and the species to which the formulation is being administered. Accordingly it is not practical to set forth generally the amount that constitutes an amount of PKC agonist effective for all possible applications. Those of ordinary skill in the art, however, can readily determine the appropriate amount with due consideration of such factors.

In certain embodiments, $CD5^+$ B cell lymphoma cells may be contacted with (a) one or more IRMs effective to increase the expression of at least one costimulatory molecule, (b) IL-2, and (c) a PKC agonist. When $CD5^+$ B cell lymphoma cells are contacted with the combination of such an IRM, IL-2, and a PKC agonist, each component of the combination may be provided in a single formulation that includes all of the components. Alternatively, the combination may be provided in two or more formulations, each of which may contain a component of the combination alone or together with one or both of the other components. If the combination is provided in a plurality of formulations, the various formulations may be of similar or dissimilar composition. Furthermore, each formulation may be of similar or dissimilar form (e.g., aerosol, gel, cream, solution, etc.) and may be administered via similar or dissimilar delivery routes (e.g., injection, transdermal, intravenous, etc). Also, if the components of the combination are provided in a plurality of formulations, the various components may be contacted with the $CD5^+$ B cell lymphoma cells in any order.

In some embodiments, a result of increasing the expression of at least one costimulatory molecule on the cell surface of $CD5^+$ B cell lymphoma cells may include increasing proliferation—i.e., expansion—of $CD5^+$ B cell lymphoma cell-specific (hereinafter, "lymphoma cell-specific") cytotoxic T cells ("CTLs"). Proliferation of lymphoma cell-specific CTLs may result from contacting lymphoma cell-specific $CD8^+$ T cells with $CD5^+$ B cell lymphoma cells having increased surface expression of costimulatory molecules. Expression of costimulatory molecules on the surface of $CD5^+$ B cell lymphoma cells may be increased by any suitable method including, for example, one or more of the methods described above.

In some embodiments, the CD8 T cells are $CD5^+$ B cell lymphoma cell-specific—i.e., $CD8^+$ T cells to which, or descendants of a $CD8^+$ T cell to which, a $CD5^+$ B cell lymphoma cell-specific antigen has previously been presented. In other embodiments, the $CD8^+$ T cells are naive—i.e., $CD8^+$ T cells to which, or descendants of a $CD8^+$ T cell to which, no antigen ($CD5^+$ B cell lymphoma-specific or otherwise) has been presented previously.

Lymphoma cell-specific CTLs activated by contact with $CD5^+$ B cell lymphoma cells having increased expression of at least one costimulatory molecule may exhibit, for example, greater proliferation than that demonstrated by lymphoma cell-specific CTLs activated by contact with $CD5^+$ B cell lymphoma cells that do not exhibit increased expression of a one or more costimulatory molecules.

In other aspects, the present invention also provides vaccines, methods of making vaccines, and methods of treating a subject by administering a vaccine. Such vaccines include isolated $CD5^+$ B cell lymphoma cells, or immunologically active portions thereof, in which the isolated $CD5^+$ B cell lymphoma cells have been contacted with an IRM effective to increase the expression of at least one costimulatory molecule on the cell surface. Isolated $CD5^+$ B cell lymphoma cells also may be contacted with IL-2, a PKC agonist, or a combination of both IL-2 and a PKC agonist. An immunologically active portion of a $CD5^+$ B cell lymphoma cell can include, but is not limited to, a cell membrane preparation and/or a protein preparation from the isolated $CD5^+$ B cell lymphoma cells. Thus, for example, a membrane preparation may include portions of the cell membrane from $CD5^+$ B cell lymphoma cells and, for example, proteins embedded therein. Vaccines may be made following any of the various procedures for the preparation of cell-based immunizations. For example, methods similar to those used for the preparation of cell-based vaccines against melanoma (see, for example, Wu et al., *J Interferon Cytokine Res.* 2001 December; 21(12): 1117-27), renal cancer cells (see, for example, Vieweg et al., *Urol. Clin. North Am.* 2003 August; 30(3):633-43) or brain tumors (see, for example, Fecci et al., *J. Neurooncol.* 2003 August-September; 64(1-2):161-76) may be used.

IRMs include compounds that possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-$\alpha$, IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,541,485; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; European Patent 0 394 026; U.S. Patent Publication Nos. 2002/0016332; 2002/0055517; 2002/0110840; 2003/0133913; 2003/0199538; and 2004/

0014779; and International Patent Publication Nos. WO 01/74343; WO 02/46749 WO 02/102377; WO 03/020889; WO 03/043572; WO 03/045391; WO 03/103584; and WO 04/058759.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in International Patent Publication No. WO 02/08905), and certain 3-β-D-ribofuranosylthiazolo[4,5-d]pyrimidine derivatives (such as those described in U.S. Publication No. 2003/0199461).

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO 00/75304.

Other IRMs include biological molecules such as aminoalkyl glucosaminide phosphates (AGPs) and are described, for example, in U.S. Pat. Nos. 6,113,918; 6,303,347; 6,525,028; and 6,649,172.

Any suitable IRM compound may be used to practice the invention. Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic mixtures of the enantiomers.

In some embodiments, a suitable IRM compound may be, for example, a small molecule IRM compound such as one of those described above. Suitable small molecule IRM compounds include those having a 2-aminopyridine fused to a five membered nitrogen-containing heterocyclic ring such as, for example, imidazoquinoline amines including but not limited to amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines including but not limited to amide substituted imidazopyridine amines, sulfonamido substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

In certain embodiments, the IRM compound can be a tetrahydroimidazoquinoline amine such as, for example, 4-amino-2-(ethoxymethyl)-α,α-dimethyl-6,7,8,9-tetrahydro-1H-imidazo[4,5-c]quinoline-1-ethanol. In alternative embodiments, the IRM compound may be an imidazoquinoline amine. In certain specific embodiments, the IRM may be 1-(2-methylpropyl)-1H-imidazo[4,5-c]quinolin-4-amine. In other embodiments, the IRM compound may be a sulfonamide substituted imidazoquinoline amine such as, for example, N-[4-(4-amino-2-ethyl-1H-imidazo[4,5-c]quinolin-1-yl)butyl]methanesulfonamide. Various combinations of IRMs can be used if desired.

The IRM compound—or each component of a combination such as, for example, an IRM and IL-2 and/or a PKC agonist—may be provided in any formulation suitable for administration to a subject. Suitable types of formulations are described, for example, in U.S. Pat. No. 5,736,553; U.S. Pat. No. 5,238,944; U.S. Pat. No. 5,939,090; U.S. Pat. No. 6,365,166; U.S. Pat. No. 6,245,776; U.S. Pat. No. 6,486,186; European Patent No. EP 0 394 026; and U.S. Patent Publication No. 2003/0199538. The compound—whether an IRM compound, IL-2, or a PKC agonist—may be provided in any suitable form including but not limited to a solution, a suspension, an emulsion, or any form of mixture. The compound may be delivered in formulation with any pharmaceutically acceptable excipient, carrier, or vehicle. For example, the compound may be provided in a formulation suitable for topical administration. Suitable types of formulations for topical delivery of, for example, certain IRM compounds are described, e.g., in International Patent Publication No. WO 03/045391. The formulation may be delivered in any conventional dosage form including but not limited to a cream, an ointment, an aerosol formulation, a non-aerosol spray, a gel, a lotion, a tablet, a lozenge, an elixir, and the like. The formulation may further include one or more additives including but not limited to adjuvants, skin penetration enhancers, colorants, fragrances, moisturizers, thickeners, and the like.

The composition of a formulation suitable for practicing the invention will vary according to factors known in the art including but not limited to the physical and chemical nature of the IRM compound, the nature of the carrier, the intended dosing regimen, the state of the subject's immune system (e.g., suppressed, compromised, stimulated), the method of administering the IRM compound, whether the IRM is being administered in combination with one or more additional agents, and the species to which the formulation is being administered. Accordingly, it is not practical to set forth generally the composition of a formulation effective for all possible applications and all possible embodiments of the invention. Those of ordinary skill in the art, however, can readily determine an appropriate formulation with due consideration of such factors.

In some embodiments, the methods of the present invention include administering IRM to a subject in a formulation of, for example, from about 0.0001% to about 10% (unless otherwise indicated, all percentages provided herein are weight/weight with respect to the total formulation) to the subject, although in some embodiments the IRM compound may be administered using a formulation that provides IRM compound in a concentration outside of this range. In certain embodiments, the method includes administering to a subject a formulation that includes from about 0.01% to about 5% IRM compound, for example, a formulation that includes about 5% IRM compound.

An amount of an IRM compound effective for practicing the invention will vary according to factors known in the art including but not limited to the physical and chemical nature of the IRM compound, the nature of the carrier, the intended dosing regimen, the state of the subject's immune system (e.g., suppressed, compromised, stimulated), the method of administering the IRM compound, whether the IRM is being administered in combination with one or more additional agents, and the species to which the formulation is being administered. Accordingly, it is not practical to set forth generally the amount that constitutes an amount of IRM compound effective for all possible applications and all possible embodiments of the invention. Those of ordinary skill in the art, however, can readily determine the appropriate amount with due consideration of such factors.

In some embodiments, the methods of the present invention include administering sufficient IRM compound to provide a dose of, for example, from about 100 ng/kg to about 50 mg/kg to the subject, although in some embodiments the methods may be performed by administering IRM compound in a dose outside this range. In some of these embodiments, the method includes administering sufficient IRM compound to provide a dose of from about 10 μg/kg to about 5 mg/kg to the subject, for example, a dose of from about 100 μg/kg to about 1 mg/kg.

The dosing regimen may depend at least in part on many factors known in the art including but not limited to the physical and chemical nature of the IRM compound, the nature of the carrier, the amount of IRM being administered, the state of the subject's immune system (e.g., suppressed, compromised, stimulated), the method of administering the IRM compound, whether the IRM is being administered in combination with one or more additional agents, and the species to which the formulation is being administered. Accordingly it is not practical to set forth generally the dosing regimen effective for all possible applications and all possible embodiments of the invention. Those of ordinary skill in the art, however, can readily determine an appropriate dosing regimen with due consideration of such factors.

In some embodiments of the invention, the IRM compound may be administered, for example, from a single dose to multiple doses per day. In certain embodiments, the IRM compound may be administered from about three times per week to about once per day. In one particular embodiment, the IRM compound is administered once per day.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

The Compounds used in the examples are shown in Table 1.

TABLE 1

| Compound | Chemical Name | Reference |
|---|---|---|
| 1RM1 | 4-amino-2-(ethoxymethyl)-α,α-dimethyl-6,7,8,9-tetrahydro-1H-imidazo[4,5-c]quinoline-1-ethanol hydrate | U.S. Pat. No. 5,352,784 Example 91 |
| IRM2 | 1-(2-methylpropyl)-1H-imidazo[4,5-c]quinolin-4-amine | U.S. Pat. No. 4,689,338 Example 99 |
| IRM3 | N-[4-(4-amino-2-ethyl-1H-imidazo[4,5-c]quinolin-1-yl)butyl]methanesulfonamide | U.S. Pat. No. 6,677,349 Example 236 |
| Negative Control (Neg.) | 4-hydroxy-1-isobutyl-1H-imidazo[4,5-c]quinoline | Example 71 of U.S. Pat. No. 4,698,348 |

Materials and Methods

Blood samples: Heparinized blood (30-40 mL) was collected from consenting CLL patients (diagnosed by a persistent elevation of $CD19^{+}CD5^{+}$ $IgM^{lo}$ lymphocytes (Rozman and Montserrat, *New Engl. J. Med.* 1995; 333:1052-1057)). All patients were untreated at the time of analysis. Protocols were approved by the appropriate Institutional Review Board.

TABLE 2

| Material | Commercial Source |
|---|---|
| Lipopolysaccharide (LPS) | Sigma Chemical Co., St. Louis, MO |
| Phorbol dibutyrate (PDB) | Sigma Chemical Co., St. Louis, MO |
| Clinical grade IL-2 | Chiron Corporation, San Francisco, CA |
| Interferon-α2b | Schering Canada, Pointe-Claire, Quebec |
| Dexamethasone | Pharmascience, Inc., Montreal, Quebec |
| Bryostatin-1 | ICN Biomedicals, Inc., Aurora, OH |
| Poly (I:C) | Amersham Pharmacia Biotech, Inc., Piscataway, NJ |
| SB203580 | Calbiochem (San Diego, CA |

Antibodies: Phycoerythrin- or FITC-labeled CD80 (B7-1), CD86 (B7-2), CD54 (ICAM-1), CD83, 4-1BB ligand (4-1BBL), CD5, and CD19 antibodies were purchased from BD Pharmingen (San Francisco, Calif.). Phycoerythrin-labeled ICOS-L and PDL-1 (B7-H1) antibodies were obtained from eBioscience (San Diego, Calif.).

Materials Preparation and Methods: Stock solutions of PDB (5 mg/mL) were made in DMSO. Stock solutions of SB203580 (25 mg/mL), an inhibitor of the selective stress-activated protein kinase (SAPK) (p38) (Lee et al., *Pharmacol Ther.* 1999; 82:389-397) were made in DMSO. IRM1 and Negative Control (Neg.) compound were provided by 3M Pharmaceuticals (St. Paul, Minn.). The compounds were dissolved in AIM-V medium (GibcoBRL, Grand Island, N.Y.) (with 33% DMSO) at 1.3 mg/mL and stored in the dark at 4° C. A 5% cream of IRM2, marketed as ALDARA, also was provided by 3M Pharmaceuticals.

Cell purification: CLL and T cells were isolated from fresh blood by negative selection (RosetteSep, StemCell Technologies, Vancouver, BC) as described by Gitelson et al. (Gitelson et al., *Clin. Cancer Res.* 2003; 99:1656-1665).

Activation of CLL cells: Purified CLL cells ($1.5\times10^{6}$ cells/mL) were cultured in serum-free AIM-V medium plus 2-mercaptoethanol (2-ME, $5\times10^{-5}$ M) (Sigma Chemical Co.) in 6- or 24-well plates (Becton-Dickinson Labware, Franklin Lake, N.J.) for 3-4 days at 37° C. in 5% $CO_2$. CLL cells were activated by adding the Negative Control compound (1

μg/mL), IRM1 (1 μg/mL), IL-2 (5000 U/mL), PDB (100 ng/mL), or bryostatin (20 nmol), as appropriate. The Negative Control compound did not have measurable effects on CLL cells and, consequently, AIM-V medium, alone, was used as a control for the majority of the experiments.

Mixed Lymphocyte Responses (MLRs): T cells were isolated from CLL patients and adjusted to $5\times10^5$ cells/mL in AIM-V medium. Activated CLL cells were washed at least 4 times to remove residual immunomodulators, irradiated (2500 cGy) and suspended at $5\times10^5$ cells/mL (or lower concentrations) in AIM-V. Responders and stimulators were then mixed in a 1:1 (vol:vol) ratio and cultured in 96-well round bottom plates (Becton Dickinson Labware, Franklin Lake, N.J.) without additional cytokines or serum. Proliferation was measured 4-6 days later using a colorimetric assay (Gitelson et al., *Clin Cancer Res.* 2003; 99:1656-1665; and Ahmed et al., *J. Immunol. Methods.* 1994; 170:211-224).

Flow cytometry: Cell staining was performed as described by Gitelson et al. (Gitelson et al., *Clin. Cancer Res.* 2003; 99:1656-1665).

Cytokine measurement: Cytokine levels in culture supernatants (from activated CLL cells after 48 hours) were determined by a multi-analysis fluorescent bead assay system available from Luminex Corp., Austin, Tex., under the tradename LUMINEX-100 SYTEM. A 5-plex human cytokine kit for IFN-γ, IL-2, IL-4, IL-10 and TNF-α measurement was used, according to the manufacturer's instructions (R&D Systems, Minneapolis, Minn.). Individual cytokine concentrations were determined from standard curves using software available from BioRad, Mississauga, Ontario, under the tradename BIO-PLEX 2.0. The assay was linear between 30 and 1000 pg/mL for each cytokine.

Statistical analysis: The Student t-test was used to determine p-values for differences between sample means. Best-fit lines were determined by least-squares regression.

Example 1

Effect of IRM1 on Costimulatory Molecule Expression by CLL Cells

CLL cells from the indicated number of patients were cultured in IRM1 (1 μg/mL) for 3-4 days, and then assayed for expression of the costimulatory molecules indicated on the x-axis (at an intensity greater than the first decade of log fluorescence) of FIG. 1A. The percentage of cells that expressed each costimulatory molecule and the mean fluorescence intensity (MFI) of expression were measured by flow cytometry. The "fold-increase" was then calculated from the ratio of these measurements to the percentage and MFI of control cells cultured without activating agents. The average and standard error of these relative increases in costimulatory molecule expression are shown in the FIG. 1A.

IRM1 has especially strong effects on CD80, CD86, and CD54 expression, with IRM1 increasing the expression of CD54, CD80, and CD86 on CLL cells from all patients studied (n=31). The effect on CD80 was greater than on CD86 (compare FIGS. 1, 2). IRM1 also increased the expression of CD83, 4-1BBL, and PDL-1, but had little effect on ICOS-L expression (FIG. 1A).

Figure 1B:
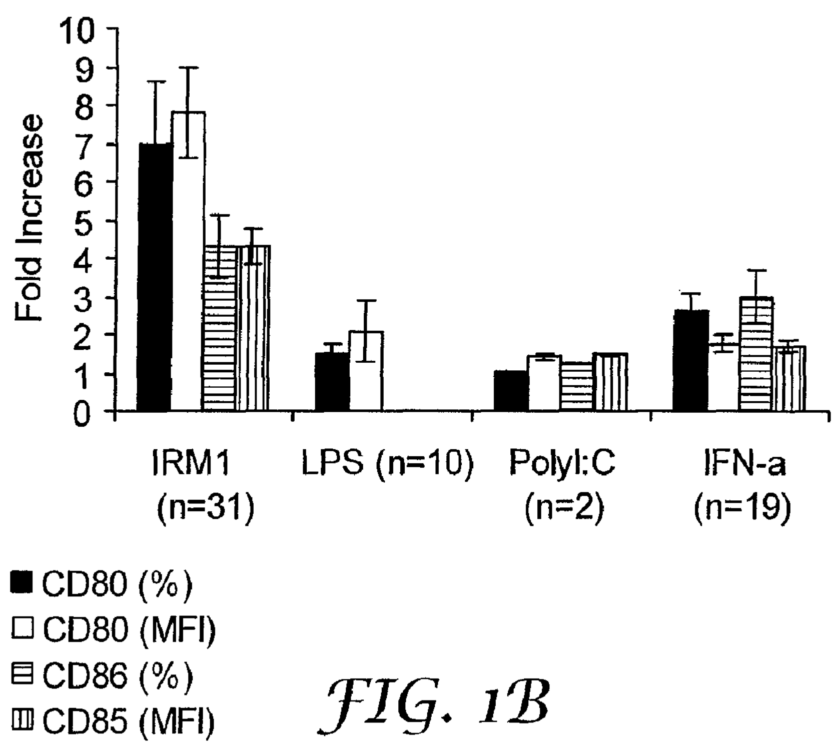

CLL cells from the indicated number of patients were cultured in IRM1, LPS (100 μg/mL), poly (I:C) (100 μg/mL) and IFN-γ 2B (500 U/mL) for 48 hours. Relative increases in the expression of CD80 and CD86 were calculated as described for FIG. 1A, and are shown in FIG. 1B.

CLL cells were not affected in the same way by other TLR agonists. TLR2 and TLR4 are activated by bacterial LPSs while TLR3 is activated by viral double-stranded RNA and poly (I:C) (Gordon, *Cell.* 2002; 111:927-930). However LPS or poly (I:C) rarely affected costimulatory molecule expression by CLL cells (FIG. 1B). Although IRM1 is one of a class of IRMs known to stimulate the release of IFN-α from DCs or monocytes (Gibson et al., *Cell Immunol.* 2002; 218:74-86), the effects of IRM1 were unlikely to be mediated indirectly by this cytokine since costimulatory molecule expression by CLL cells did not change significantly after direct stimulation with IFN-γ2B (FIG. 1B).

Example 2

Effects of IL-2 and IRM1 on Costimulatory Molecule Expression by CLL Cells

Figure 2A:
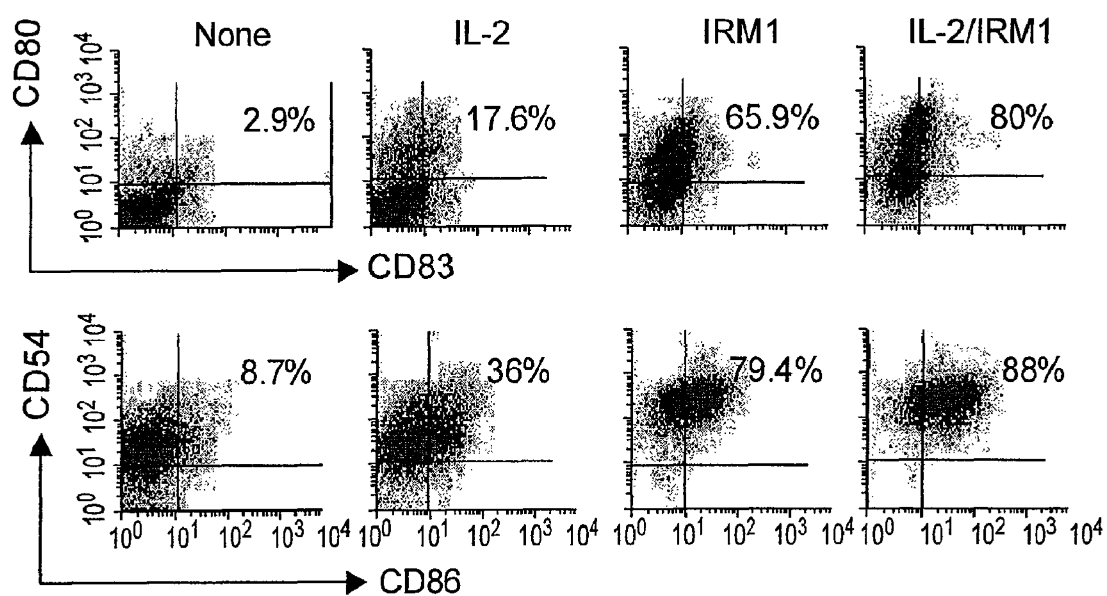
FIGS. 2A-C. Effect of an IRM compound (with or without IL-2) on costimulatory molecule expression by CLL cells.
Figure 2B:
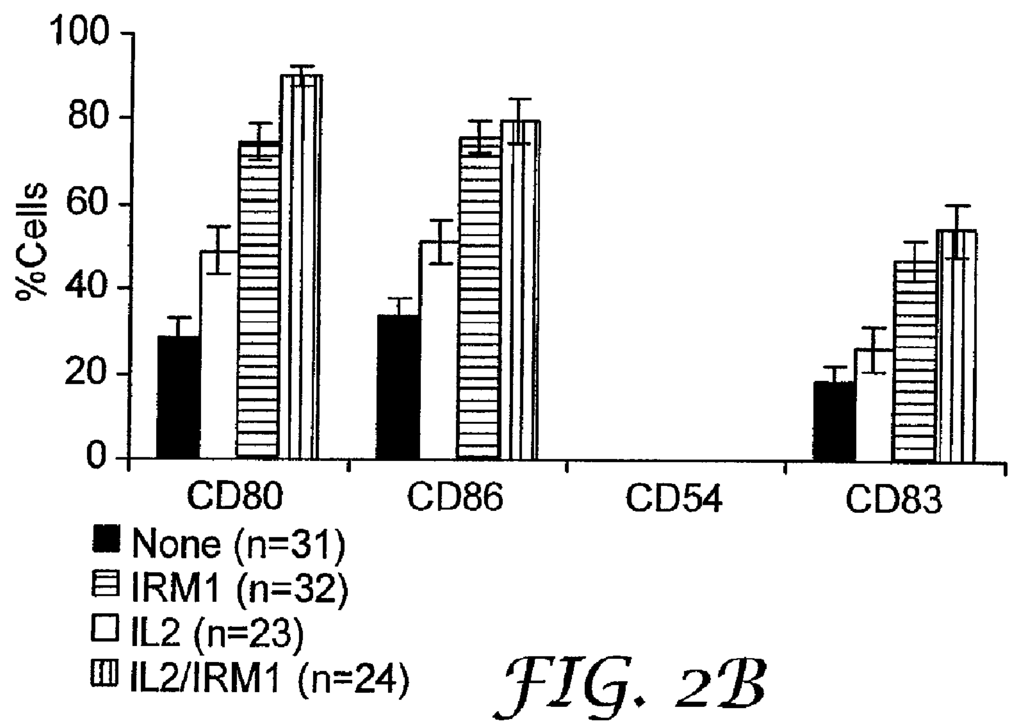
Figure 2C:
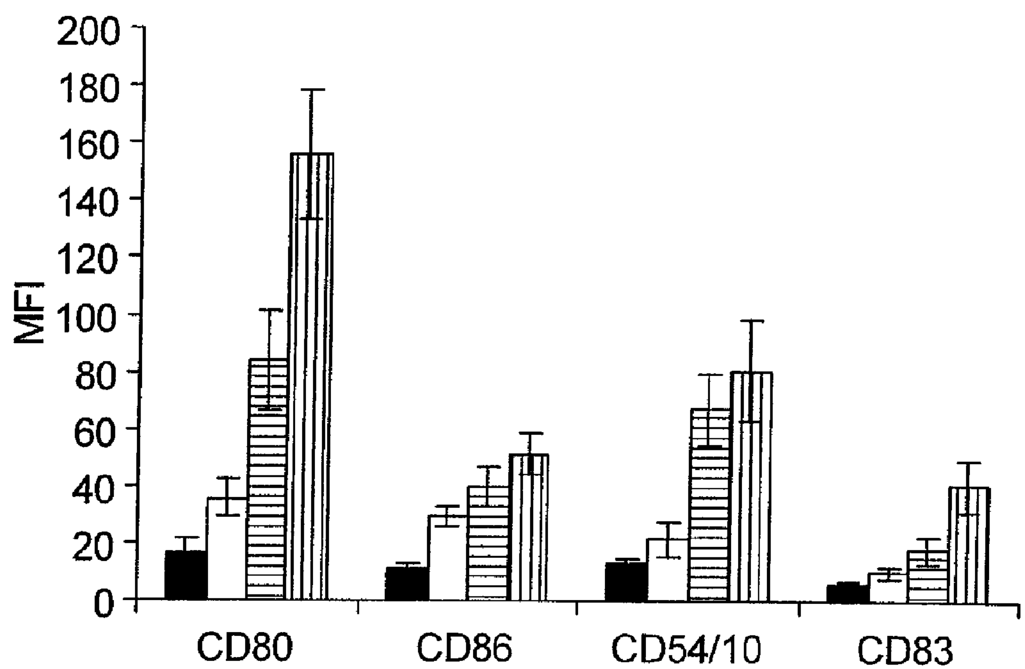

CLL cells were isolated and cultured alone or with IL-2 (5000 U/mL), IRM1 (1 μg/mL), or both IL-2 and IRM1 for 3-4 days. The expression of CD80, CD86, CD54, and CD83 was then determined by flow cytometry. FIG. 2A shows a characteristic example. The numbers in the dot plots in the upper and lower rows are the percentages of $CD80^+$ and $CD86^+$ CLL cells, respectively. FIG. 2B is a graphical representation of the percentage of CLL cells expressing the different costimulatory molecules (determined by the percentage of cells with staining intensity above the first decade of log fluorescence) from the number of patients indicated in the graph legend. The average and standard error for each of these measurements are shown in the graphs. The numbers over the double-headed arrows represent the p-values for the differences between sample means. FIG. 2C is a graphical representation of the mean fluorescence index (MFI) of expression of the different costimulatory molecules determined for CLL cells from the number of patients indicated in the graph legend. The average and standard error for each of these measurements are shown in the graphs. Only the MFI of CD54 expression (divided by 10) is shown since essentially all CLL cells express this molecule. The numbers over the double-headed arrows represent the p-values for the differences between sample means.

IL-2 and IRM1 both increased the percentage of CLL cells that expressed CD80 and CD86, as well as the mean fluorescence intensity (MFI) of expression of these molecules (FIG. 2). As a single agent, IRM1 appeared to be more potent than IL-2 in this regard. The effects of IL-2 and IRM1 on costimulatory molecule expression were additive (FIG. 2A, right dot-plots and FIGS. 2B,C), suggesting they were mediated by different mechanisms. The MFI for the costimulatory molecules CD80, CD86, CD54, and CD83 shown in FIG. 2C indicate that IRM1 increased the expression of all four of these costimulatory molecules on CLL cells. The magnitude of CD80 expression was especially increased by IRM1 in combination with IL-2.

Expression of 4-1BBL and PDL-1 was increased somewhat by IL-2 and IRM1, but not as much as CD80, CD86, and CD54 (FIG. 1A). ICOS-L was found on many CLL cells but its expression appeared to be relatively independent of IL-2 and IRM1-mediated signaling.

Example 3

Figure 3A:
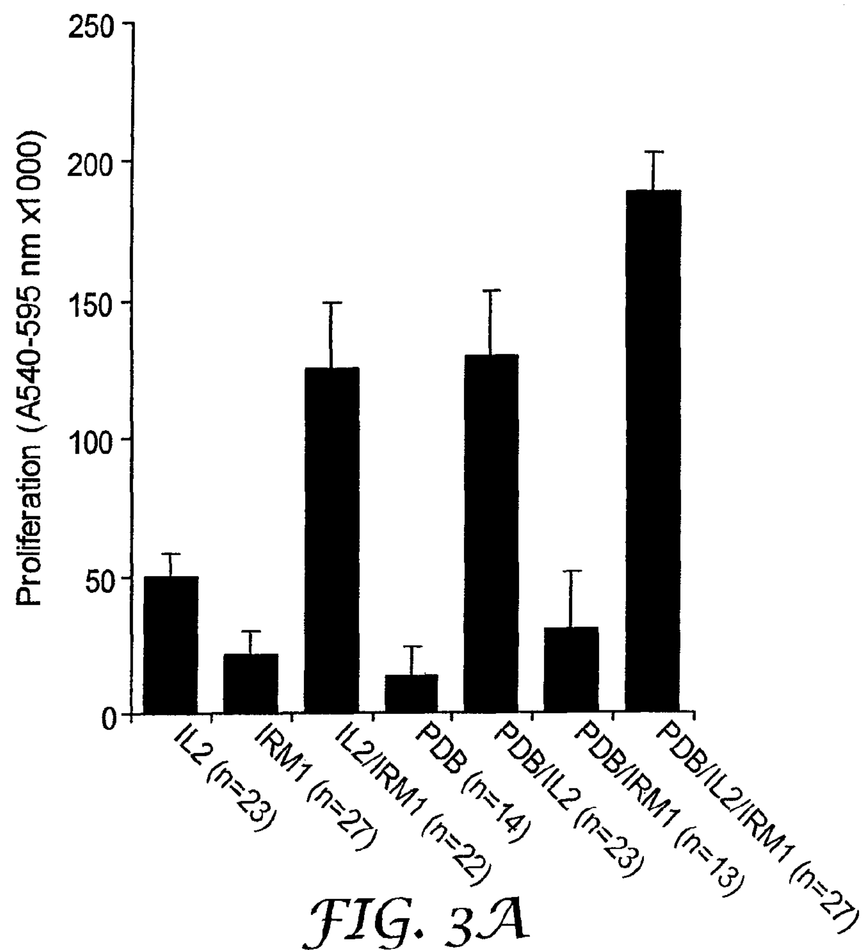
FIGS. 3A-B. Effect of an IRM compound on the ability of CLL cells to stimulate cytotoxic T cell proliferation.

Effect of PKC Activation on Costimulatory Phenotype and T Cell Stimulatory Ability of IL-2- and IRM1-Activated CLL Cells CLL cells were purified from individual patients and cultured alone or with IL-2, IRM1, IL-2 and IRM1, PDB, PDB and IL-2, PDB and IRM1, or PDB, IL-2, and IRM1. After 3-4 days, these cells were harvested, washed extensively, irradiated (2500 cGy) and used to stimulate allogenic or autologous T cells from CLL patients (obtained at the same time as the CLL cells and rested in culture until added to the Mixed Lymphocytic Response (MLR) assay) after 5-6 days of culture, alamar blue was added and proliferation was measured in an optical density calorimetric microplate reader at wavelengths of 540 (reduced state) and 595 (oxidized state). The difference between these readings was used as a measure of the number of viable cells in the culture. Results are shown in FIG. 3A. The results from the T cell source that exhibited the greatest stimulation (after subtraction of the proliferation induced by non-activated CLL cell stimulators) from each individual experiment were used to generate the average proliferation and standard error from the number of patients indicated on the x-axis.

Figure 3B:
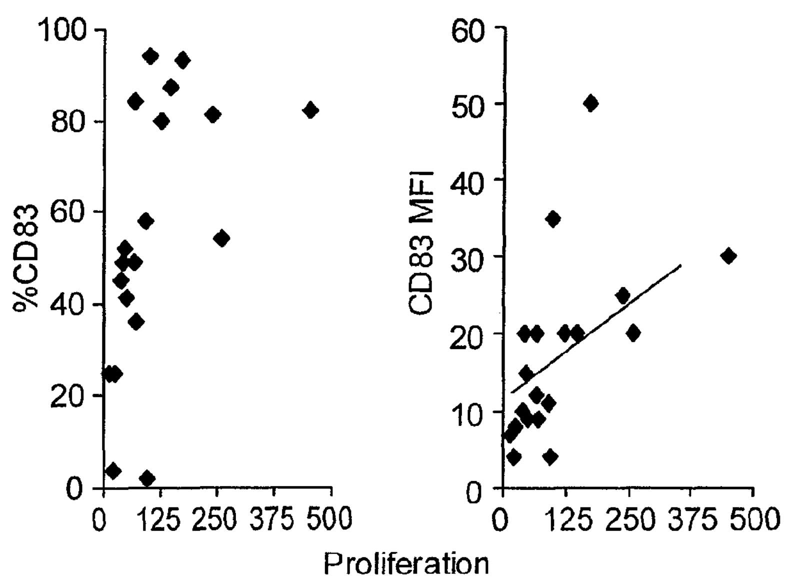

FIG. 3B is a graphical representation of the correlation of CD83 expression with T cell stimulatory ability. CLL cells were treated with IL-2 and IRM1 for 4-5 days. The percentage of cells expressing CD83 and the MFI of CD83 expression were then determined by flow cytometry. The activated CLL cells were then irradiated and used to stimulate autologous or allogeneic T cells in MLRs. The initial percentages of $CD83^+$ CLL cells (left panel) and the MFI of CD83 expression (right panel) from 19 different patients were then correlated with the measured proliferation in the MLRs. The best straight line has intercept 10.692 and slope 0.0598; the associated P-value is 0.0153.

Figure 4A:
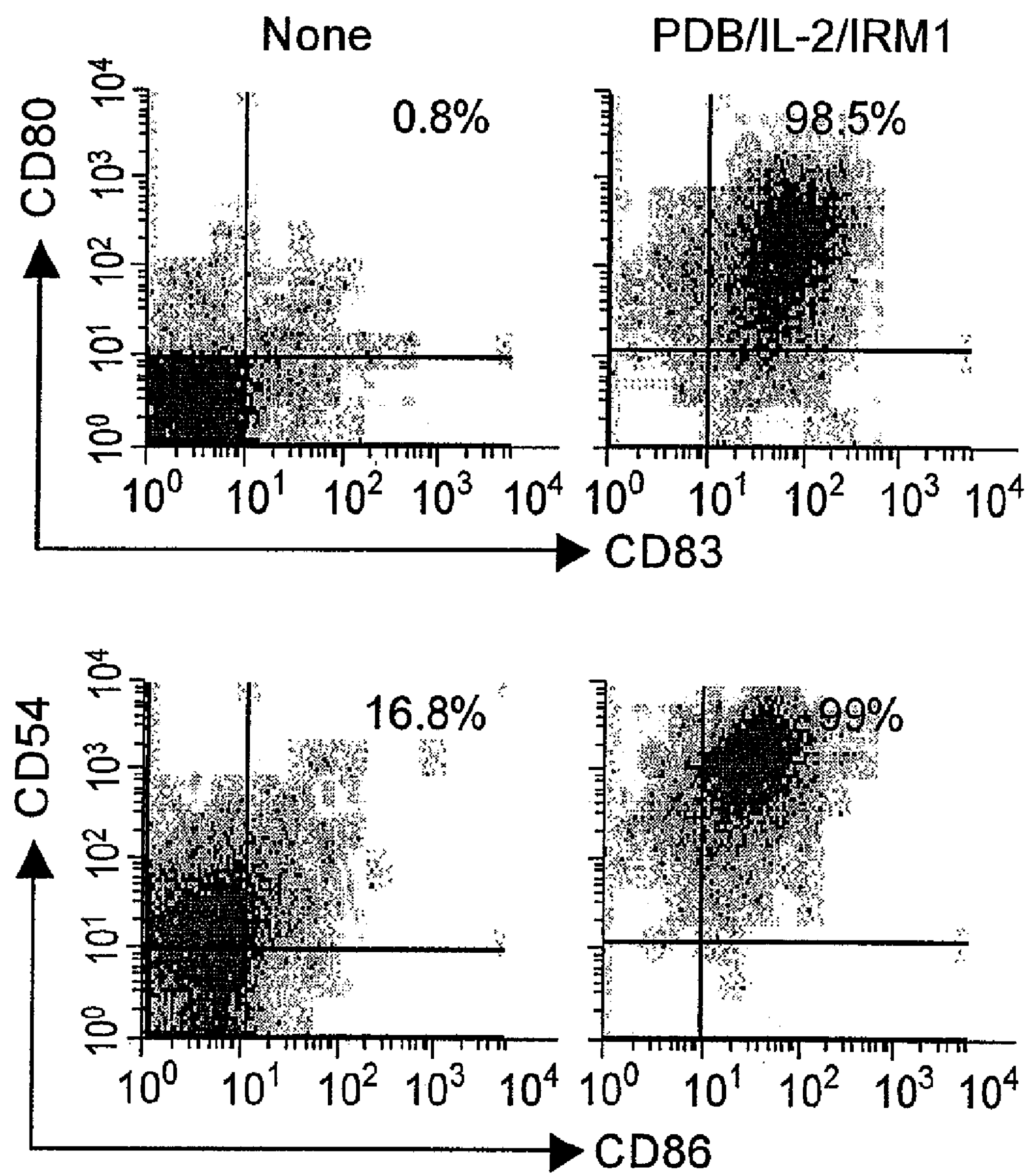
FIGS. 4A-C. Effect of an IRM compound, IL-2, and PKC agonists on costimulatory molecule expression by CLL cells.
Figure 4B:
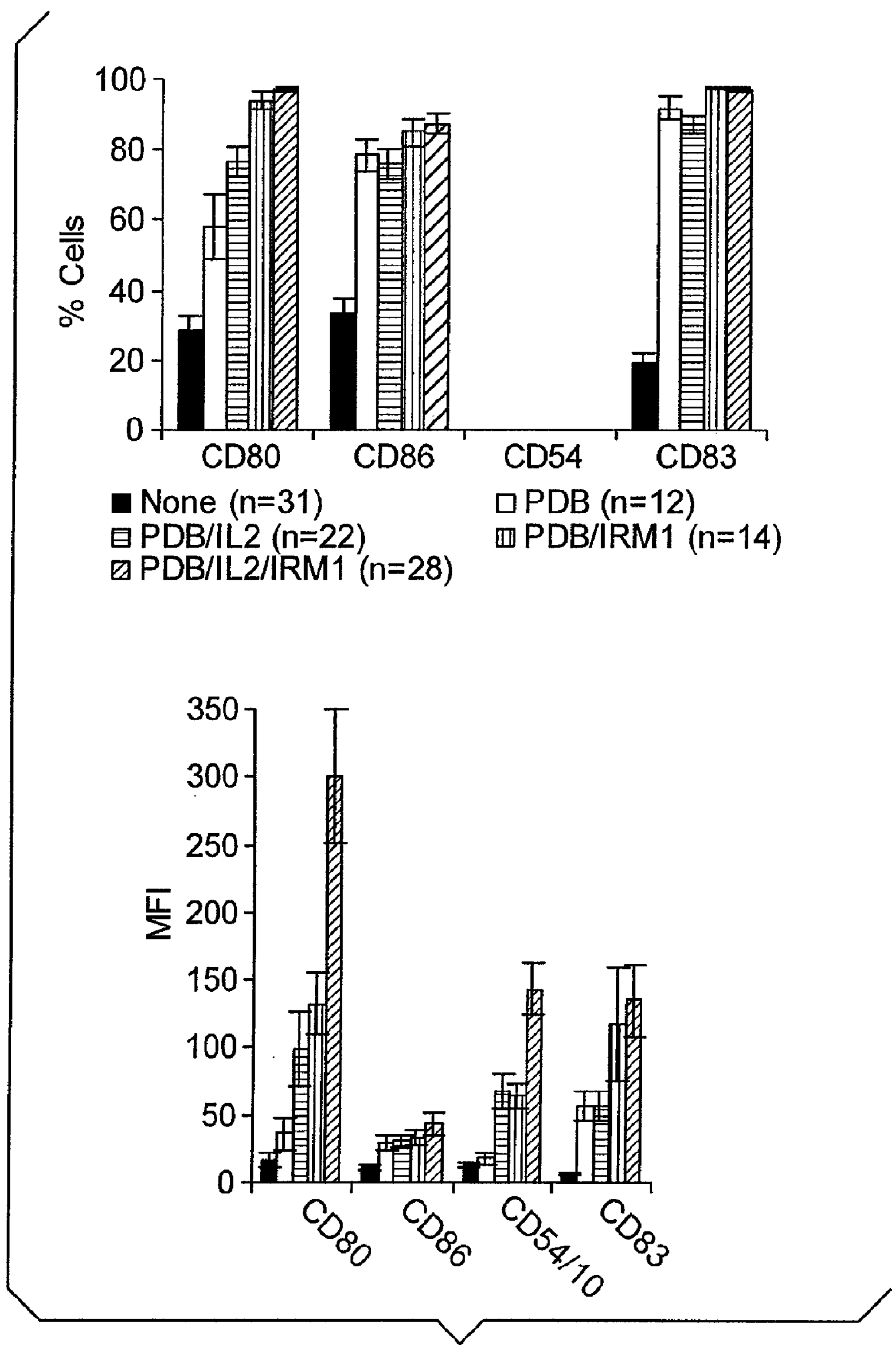
Figure 4C:
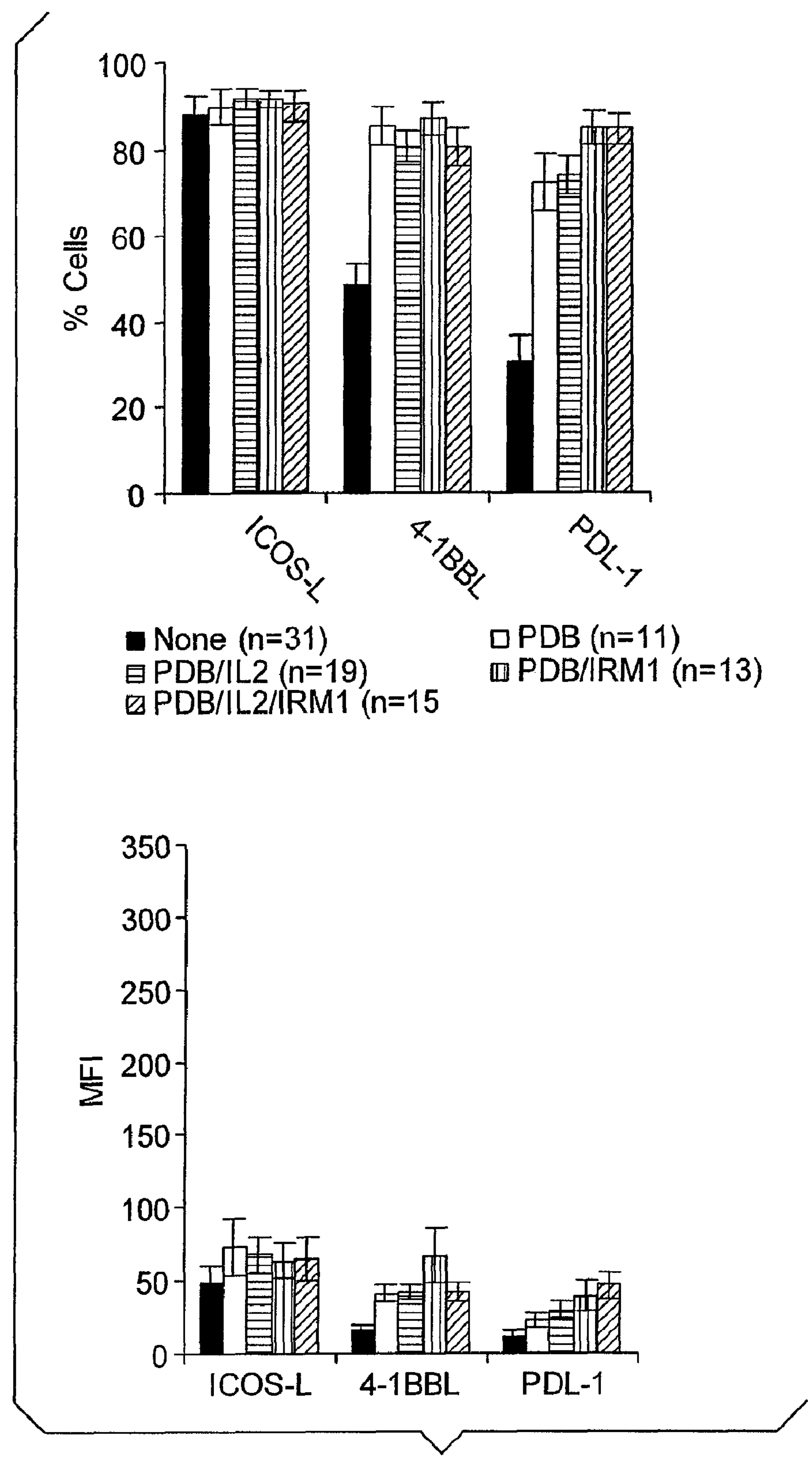

FIG. 4A shows CLL cells from a representative patient that were cultured alone (left panels) or with IRM1, IL-2, and PDB (right panels) for 3 days. CD80, CD83, CD54, and CD86 expression were then determined by flow cytometry. The percentages in the dot-plots refer to CD80 (sum of the right and left upper quadrants) (top panels) and to CD86 (sum of the right upper and lower quadrants) (bottom panels). FIG. 4B is a summary of the results of flow cytometric evaluation of the percentage of CLL cells expressing CD80, CD83, CD54, and CD86 (and the MFI of expression) after culture alone, with PDB, PDB and IL-2, PDB and IRM1, or PDB, IL-2 and IRM1 from the indicated number of patients in the graph legend. The average and standard error are shown. Only the MFI of CD54 expression is shown since essentially all CLL cells express this molecule. FIG. 4C is a summary of similar flow cytometric evaluation of ICOS-L, 4-1BBL, and PDL-1 expression. The numbers over the double-headed arrows are the p-values for the differences between sample means.

Treatment with phorbol dibutyrate (PDB), alone, caused ~90% of CLL cells to express CD83 (FIG. 4B, clear bars). PDB also increased the number of $CD80^+$ and $CD86^+$ CLL cells (the latter more than the former), as well as the expression of 4-1BBL and PDL-1 (FIG. 4C, clear bars): CD54 and ICOS-L expression were not affected greatly by PDB (FIG. 4B and FIG. 4C).

Addition of IL-2 during activation of CLL cells with PDB increased mainly the number of $CD80^+$ cells and the MFI of CD80 and CD54 expression (FIG. 4B; horizontal bars). A slightly greater percentage of $CD80^+$ cells was obtained when CLL cells were activated with both PDB and IRM1 (FIG. 4B; vertical bars). The addition of IL-2 to IRM1 and PDB strongly increased the expression of CD80 (especially compared to CD86 (FIG. 4B)), as well as CD54, and caused essentially all CLL cells to acquire a $CD83^{hi}CD80^{hi}CD86^{hi}CD54^{hi}$ cell surface phenotype (FIG. 4A and FIG. 4B; diagonal bars).

The results shown in FIG. 4 indicated that the combination of PDB and IRM1 caused nearly 100% of CLL cells to acquire CD80, CD86, and CD83 expression. The addition of IL-2 affected mainly the magnitude of CD80 and CD54 expression. PDB, with or without IL-2, and/or IRM1 increased the expression of 4-1BBL and PDL-1 but not to the same extent as CD80, CD86, CD54, and CD83.

This strong expression of costimulatory molecules by CLL cells activated with PDB, IL-2, and IRM1 was reflected in the ability of these cells to stimulate T cell proliferation (FIG. 3A). CLL cells stimulated with PDB (without IL-2) were weak stimulators of T cell proliferation (FIG. 3A).

Example 4

Elimination of CLL Cells by Autologous T Cells in the Presence of IRM1

Figure 5A:
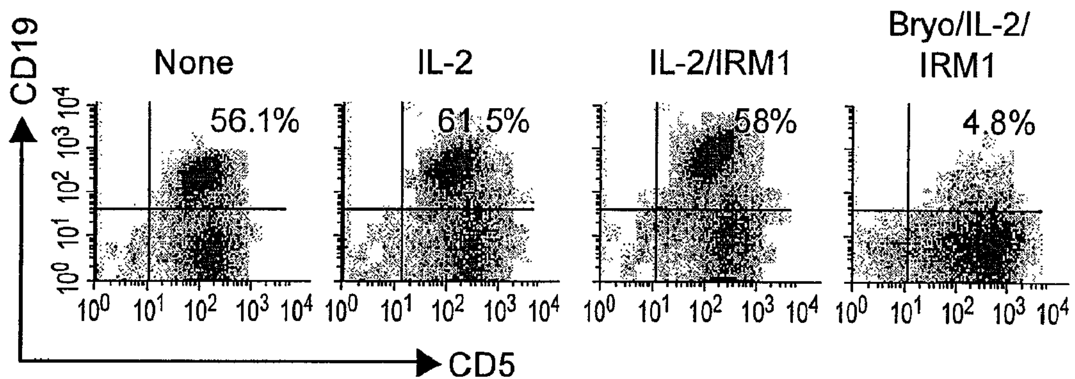
FIGS. 5A-B. Induction of T cell cytotoxicity against autologous CLL cells by PKC agonists, IL-2, and IRM.
Figure 5B:
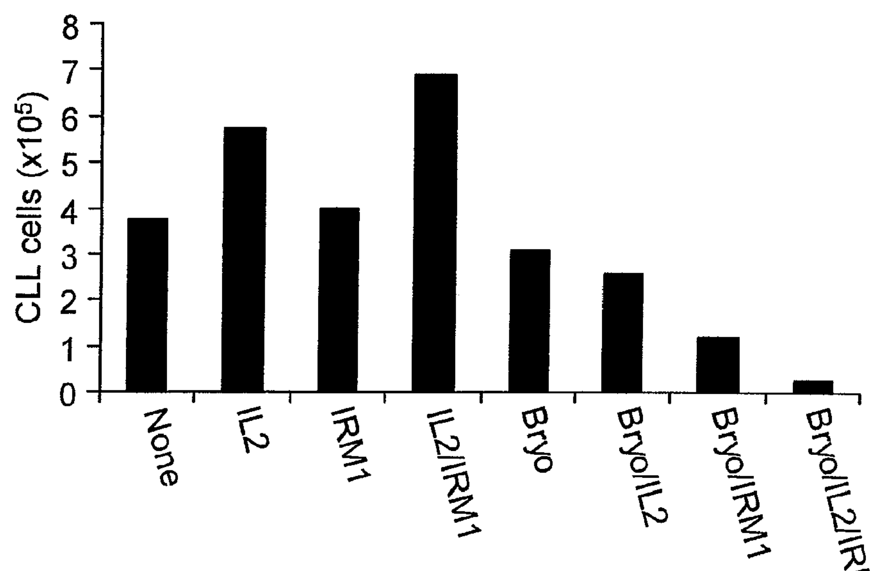

CLL cells and T cells were isolated from a CLL patient, suspended at concentrations of $10^6$ cells/mL and mixed in a 1:1 ratio. The cell mixtures were cultured alone, or in the presence of IL-2, IL-2 and IRM1, bryostatin, bryostatin and IL-2, bryostatin and IRM1, or bryostatin, IL-2, and IRM1. In FIG. 5A, after 5 days, the percentages of $CD5^+$ $CD19^+$ tumor cells (indicated by the numbers in the right upper quadrants of the dot-plots) and $CD5^+$ $CD19^-$ T cells were determined by flow cytometry. In FIG. 5B, these percentages and the total numbers of viable cells (determined by manual counting in a hemocytometer) were used to calculate the remaining absolute numbers of CLL cells in the cultures.

IRM1, whether alone or in combination with IL-2 and/or bryostatin, induced autologous T cells to kill CLL cells in vitro. The combination of IRM1, IL-2, and bryostatin enabled autologous T cells to achieve 100% clearance of CLL cells in 5 days.

Example 5

Clinical Effects of Administering an IRM Compound to Lymphomatous Skin Deposits Associated with Chronic Lymphocytic Leukemia A 71-year old Caucasian male was diagnosed with Rai Stage 0 CLL on the basis of a persistent elevated count of circulating monoclonal $CD19^+$ $CD5^+$ $IgM^{lo}$ lymphocytes, determined by flow cytometry. CD38 was expressed by 45% of circulating CLL cells. The white blood cell counts at the beginning and end of treatment with IRM2 were $36\times10^6$ cells/mL and $45\times10^5$ cells/mL, respectively. Other systemic chemotherapy, steroids, or radiation had not been administered previously.

Figure 8A:
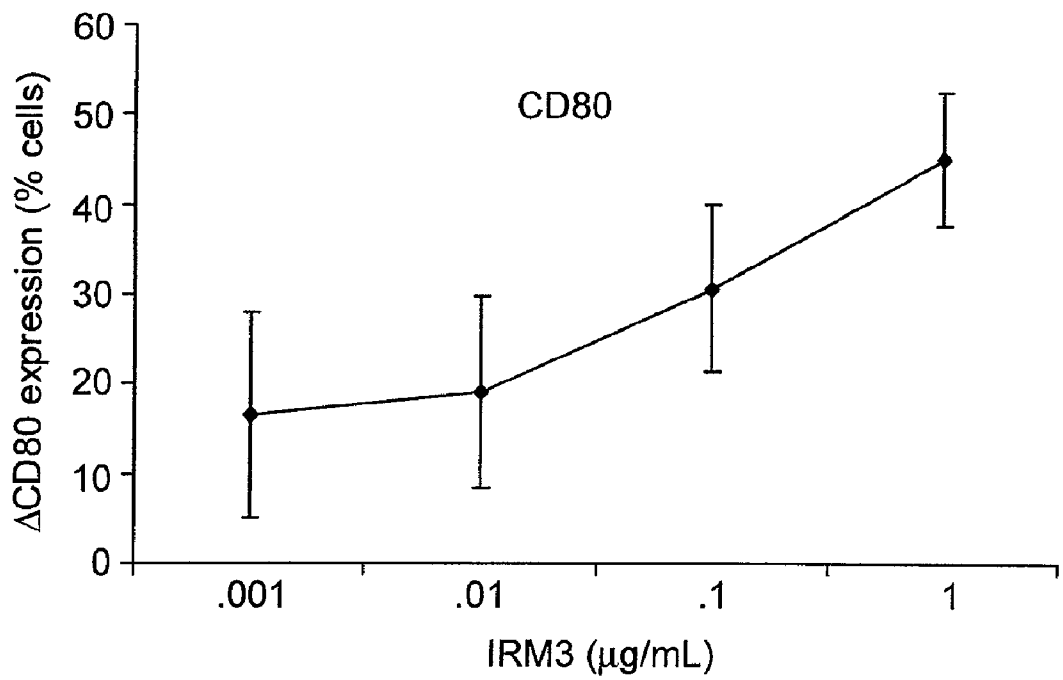
FIG. 8A-B. Effect of IRM3 on expression of CD80 and CD83 by CLL cells.

Additionally, the patient reported having recurrent nodular, erythematous lesions on his hands and arms for approximately eight years. The lesions were usually removed by treatment with liquid nitrogen. At the time he was diagnosed with CLL, he had several such lesions over his upper back (FIG. 8A) and arms. One lesion was biopsied and found to contain a diffuse atypical lymphoid dermal infiltrate consisting of many small, round lymphocytes, without epidermotropism. On paraffin immunoperoxidase stains, the lymphoid filtrate had a predominant $CD20^+$ phenotype. Molecular analysis on paraffin embedded tissue demonstrated a monoclonal B cell population, consistent with B cell lymphoma.

A 5% cream of IRM2 was applied to the affected area three times per week. After eight weeks, the size of the treated lesion had not changed significantly, although an area of hypopigmentation had formed that was reminiscent of a halo nevus around a regressing melanoma deposit.

Administration of 5% IRM2 cream was increased to once per day. The lesion disappeared after six weeks of treatment (FIG. 6B) and had not recurred by three months after treatment ceased. Neither untreated lymphomatous lesions nor circulating white blood cell count changed significantly over the course of the treatment.

CLL cells were isolated from fresh blood by negative selection (RosetteSep, StemCell Technologies, Inc., Vancouver, BC) as described in Gitelson et al., *Clin. Can. Res.,* 9:1656-1665 (2003). Purified CLL cells ($1.5\times10^6$ cells/mL) were cultured in serum-free AIM-V medium (GibcoBRL) for three days. IRM1 and Negative Control compound were used at final concentrations of 1 μg/mL.

Cells were incubated with pre-optimized volumes of either CD80-PE and CD83-FITC or CD54-PE and CD86-FITC antibodies for 20 minutes, washed, then subjected to flow cytometry analysis. Negative controls were isotype-matched irrelevant antibodies. Staining of nucleated cells was determined by gating on forward- and side-scatter properties. Ten thousand viable counts were analyzed with a FACScan flow cytometer using CELLQUEST software (BD Immunocytometry Systems, San Jose, Calif.). The flow cytometer was standardized with SpheroParticles (Spherotech, Inc., Chicago, Ill.). Percentages of $CD80^+$, $CD86^+$, and $CD83^+$ cells were calculated by comparison with isotype control-labeled cells. Results are shown in FIG. 7.

Example 6

Dose Response of IRM3 Effects on Costimulatory Marker Expression by CLL Cells

Figure 8B:
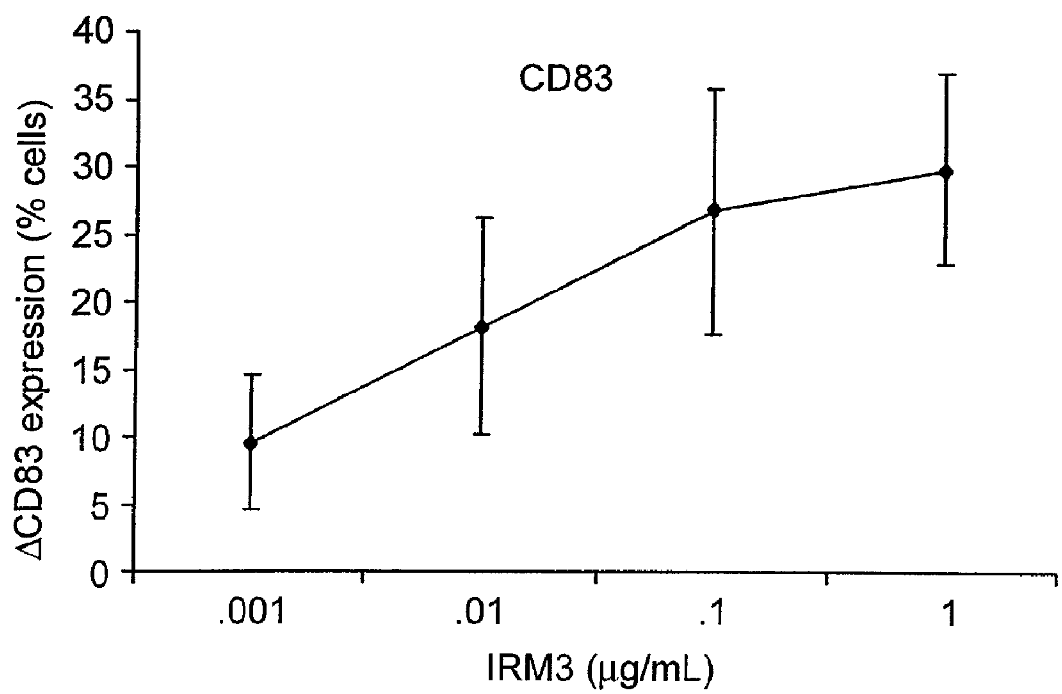

CLL cells from eight different patients were purified and cultured with either 0.001 μg/mL, 0.01 μg/mL, 0.1 μg/mL, or 1.0 μg/mL of IRM3 for three days. CD80 and CD83 expression was determined by flow cytometry as described above. Increases in CD80 and CD83 expression were computed by subtracting CD80 and CD83 expression, respectively, from control CLL cultures to which no IRM3 was added. Results are presented in FIG. 8.

Example 7

IRM3-Mediated Changes in CLL Cell Surface Molecules

Figure 9:
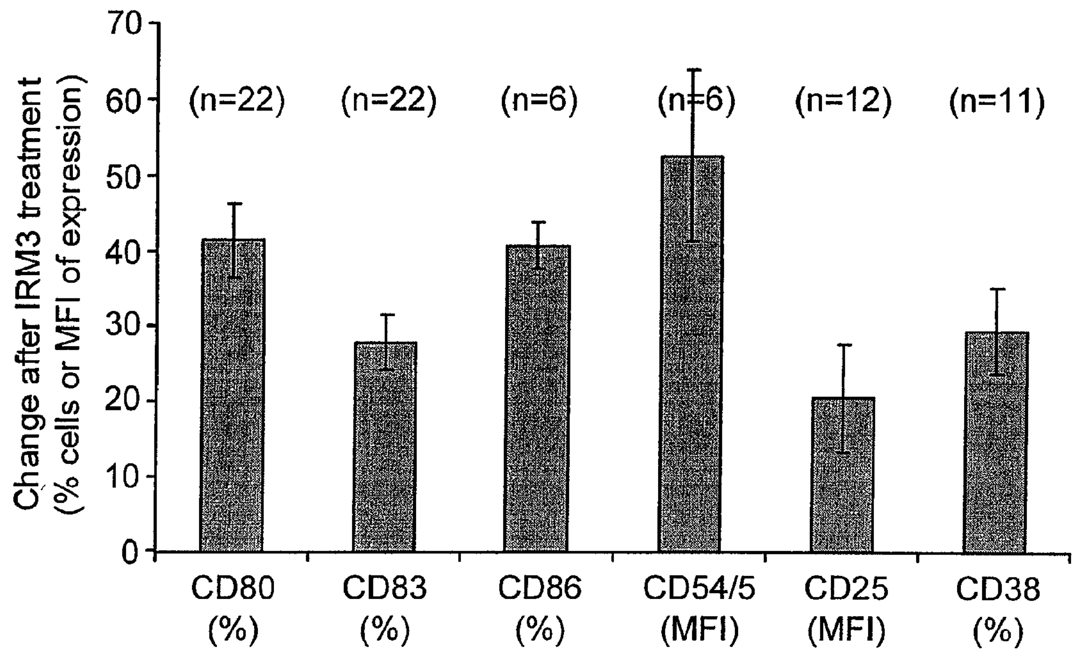
FIG. 9. IRM3-Mediated changes in cell surface molecule expression in CLL cells.

CLL cells were collected from patients and cultured for 2-3 days with IRM3 (1 μg/mL) and without (control). The percentages of cells that expressed CD80, CD83, CD86, and CD38 were determined by flow cytometry. The MFI of expression of CD54 and CD25 was determined because virtually all CLL cells express these molecules. Changes in MFI of expression or the percentage of cells expressing a particular cell surface molecule were determined by subtracting values obtained from control cultures from the values obtained from cells cultured with IRM3. Results are presented in FIG. 9.

Example 8

IRM3-Mediated Increase in Expression of CD20 by CLL Cells

Figure 10:
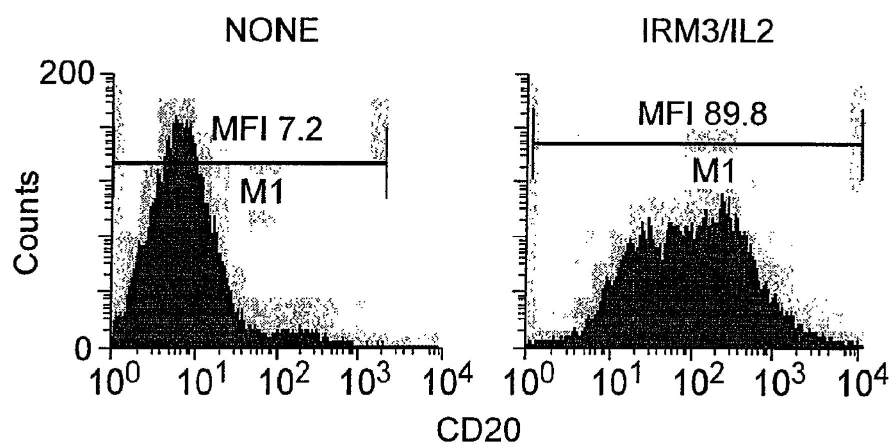
FIG. 10. IRM3+IL-2 increases expression of CD20 on CLL cells.

CLL cells were purified and cultured either without (control) or with IRM3 (1 μg/mL) and IL-2 (5000 U/mL). After 48 hours, the MFI of CD20 expression was determined by flow cytometry. Results are presented in FIG. 10.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of treating a subject with a $CD5^+$ B cell lymphoma, the method comprising administering to the subject an IRM, wherein the IRM is 4-amino-2-(ethoxymethyl)-α,α-dimethyl-6,7,8,9-tetrahydro-1H-imidazo[4,5-c]quinoline-1-ethanol;

1-(2-methylpropyl)-1H-imidazo[4,5-c]quinolin-4-amine; or

N-[4-(4-amino-2-ethyl-1H-imidazo[4,5-c]quinolin-1-yl) butyl]methanesulfonamide.

2. The method of claim 1, wherein the IRM is N-[4-(4-amino-2-ethyl-1H-imidazo[4,5-c]quinolin-1-yl-butyl]methanesulfonamide.

3. The method of claim 1, wherein the IRM is 1-(2-methylpropyl)-1H-imidazo[4,5-c]quinolin-4-amine.

4. The method of claim 1, wherein the IRM is 4-amino-2-(ethoxymethyl)-α,α-dimethyl-6,7,8,9-tetrahydro-1H-imidazo[4,5-c]quinoline-1-ethanol.

* * * * *